US007776827B2

(12) United States Patent
Siegel

(10) Patent No.: US 7,776,827 B2
(45) Date of Patent: Aug. 17, 2010

(54) METHOD OF USING SUBSTANCE P ANALOGS FOR TREATMENT AMELIORATION OF MYELODYSPLASTIC SYNDROME

(75) Inventor: Hal Siegel, Paradise Valley, AZ (US)

(73) Assignee: ImmuneRegen Biosciences, Inc., Scottsdale, AZ (US)

(*) Notice: Subject to any disclaimer, the term of this patent is extended or adjusted under 35 U.S.C. 154(b) by 16 days.

(21) Appl. No.: 12/179,416

(22) Filed: Jul. 24, 2008

(65) Prior Publication Data
US 2009/0075903 A1 Mar. 19, 2009

Related U.S. Application Data

(60) Provisional application No. 60/952,394, filed on Jul. 27, 2007, provisional application No. 61/039,867, filed on Mar. 27, 2008.

(51) Int. Cl.
*A61K 38/08* (2006.01)
(52) U.S. Cl. ....................................................... 514/15
(58) Field of Classification Search ........................ None
See application file for complete search history.

(56) References Cited

U.S. PATENT DOCUMENTS

| 5,359,030 | A | 10/1994 | Ekwuribe |
| 5,438,040 | A | 8/1995 | Ekwuribe |
| 5,681,811 | A | 10/1997 | Ekwuribe |
| 6,191,105 | B1 | 2/2001 | Ekwuribe et al. |
| 6,309,633 | B1 | 10/2001 | Ekwuribe et al. |
| 6,380,405 | B1 | 4/2002 | Ekwuribe et al. |

OTHER PUBLICATIONS

Bardelli et al., 2005, "Expression of Functional NK1 Receptors in Human Alveolar Macrophages: Superoxide Anion Production, Cytokine Release and Involvement of NF-kB Pathway," British Journal of Pharmacology, vol. 145:385-396.
Berger et al., 1979, "Substance P: In Vitro Inactivation by Rat Brain Fractions and Human Plasma," Biochemical Pharmacology, vol. 28:3173-3180.
Blumberg and Teichberg, 1979, "Biological Activity and Enzymic Degradation of Substance P Analogs: Implications for Studies of the Substance P Receptor," Biochemical Biophysical Research Communications, vol. 90(1):347-354.
Broome and Miyan, 2000, "Neuropeptide Control of Bone Marrow Neutrophil Production: A Key Axis for Neuroimmunomodulation," Ann. NY Acad. Sci., vol. 917:424-434.
Catnach et al., 1994, "Intestinal Absorption of Peptide Drugs: Advances in Our Understanding and Clinical Implications," Gut, vol. 35(4):441-444.
Chernova et al., 2009, Substance P Enhances CCL5-Induced Chemotaxis and Intracellular Signaling in Human Monocytes, Which Express the Truncated Neurokinin-1 Receptor, Journal of Leukocyte Biology, vol. 85:1-11.

Economopoulos et al., 1996, "Treatment of High Risk Myelodysplastic Syndromes with Idarubicin and Cytosine Arabinoside Supported by Granulocyte-Macrophage Colony-Stimulating Factor (GM-CFS)," Leukemia Research, vol. 20(5):385-390.
Goode et al., 2000, "Differential Expression of Neurokinin-1 Receptor by Human Mucosal and Peripheral Lymphoid Cells," Clinical and Diagnostic Laboratory Immunology, vol. 7:371-376.
Greco et al., 2004, "Tachykinins in the Emerging Immune System: Relevance to Bone Marrow Homeostatis and Maintenance of Hematopoietic Stem Cells," Frontiers in Bioscience, vol. 9:1782-1793.
Hiramoto et al., 1998, "Stimulatory Effects of Substance P On CD34 Positive Cell Proliferation and Differentiation in Vitro are Mediated by the Modulation of Stromal Cell Function," International Journal of Molecular Medicine, vol. 1:347-354.
Joshi et al., 2001, "Negative Feedback on the Effects of Stem Cell Factor on Hematopoiesis is Partly Mediated Through Neutral Endopeptidase Activity on Substance P: A Combined Functional Proteomic Study," Blood, vol. 98:2697-2706.
Lai et al., 1998, "Human Lymphocytes Express Substance P and its Receptor," Journal of Neuroimmunology, vol. 86:80-86.
Lai et al., 2006, "Full-Length and Truncated Neurokinin-1 Receptor Expression and Function During Monocyte/Macrophage Differentiation," PNAS, vol. 103:7771-7776.
Li et al., 2000, "Human Stem Cells Express Substance P Gene and Its Receptor," Journal of Hematotherapy and Stem Cell Research, vol. 9:445-452.
Neumeister et al., 2002, "Myelodysplactic Syndrome," American Journal of Cancer, vol. 1(5):301-311.
Nowicki et al., 2008, "In Vitro Substance P-Dependent Induction of Bone Marrow Cells in Common (CD10) Acute Lympholastic Leukemia," Leukemia Research, vol. 32: 97-102.
Patel et al., 2007, "An In Vitro Method to Study the Effects of Hematopoietic Regulators During Immune and Blood Cell Development," Biol. Proced. Online, vol. 9:56-64.
Rameshwar et al., 1993, "In Vitro Stimulatory Effect of Substance P on Hematopoiesis," Blood, vol. 81(2):391-398.
Rameshwar et al., 1997, "Hematopoietic Regulation Mediated by Interactions Among the Neurokinins and Cytokines," Leukemia and Lymphoma, vol. 28:1-10.
Rameshwar, P., 1997, "Substance P: A Regulatory Neuropeptide for Hematopoiesis and Immune Functions," Clinical Immunology and Immunopathology, vol. 85:129-133.
Rameshwar et al., 1997, "Receptor Induction Regulates the Synergistic Effects of Substance P with IL-1 and Platelet-Derived Growth Factor on the Proliferation of Bone Marrow Fibroblasts," Journal of Immunology, vol. 158:3417-3424.
Rameshwar et al., 2001, "Mimicry Between Neurokinin-1 and Fibronectin May Explain the Transport and Stability of Increased Substance P Immunoreactivity in Patients with Bone Marrow Fibrosis," Blood, vol. 97:3025-3031.

(Continued)

*Primary Examiner*—Christina Bradley
(74) *Attorney, Agent, or Firm*—Jones Day

(57) ABSTRACT

Myelodysplastic syndromes can be treated or ameliorated by the administration of substance P analogs as disclosed herein.

15 Claims, 3 Drawing Sheets

OTHER PUBLICATIONS

Rameshawar et al., 2001, "The Dynamics of Bone Marrow Stromal Cells in the Proliferation of Multipotent Hematopoietic Progenitors by Substance P: an Understanding of the Effects of a Neurotransmitter on the Differentiating Hematopoietic Stem Cell," Journal of Neuroimmunology, vol. 121:22-31.

Rameshawar et al., 2002, "Structural Similarity Between the Bone Marrow Extracellular Matrix Protein and Neurokinin 1 Could be the Limiting Factor in the Hematopoietic Effects of Substance P," Can. J. Physiol. Pharmacol., vol. 80:475-481.

Rich, R., 2003, "In Vitro Hematotoxicity Testing in Drug Development: A Review of Past, Present and Future Applications," Current Opinion in Drug Discovery Development, vol. 6:100-109.

Rich and Hall, 2005, "Validation and Development of a Predictive Paradigm for Hemotoxicology Using a Multifunctional Bioluminescence Colony-Forming Proliferation Assay," Toxicological Sciences, vol. 87(2):427-441.

Shue et al., 2006, "Cyclic Urea Derivatives as Potent NK Selective Antagonists. Part II: Effects of Fluoro and Benzylic Methyl Substitutions," Bioorganic & Medicinal Chemistry Letters, vol. 16(4):1065-1069.

Fig. 1 Colony count of BFU-E vs. concentration for HOMSPERA® (Sar$^9$-SP) and substance P (SP).
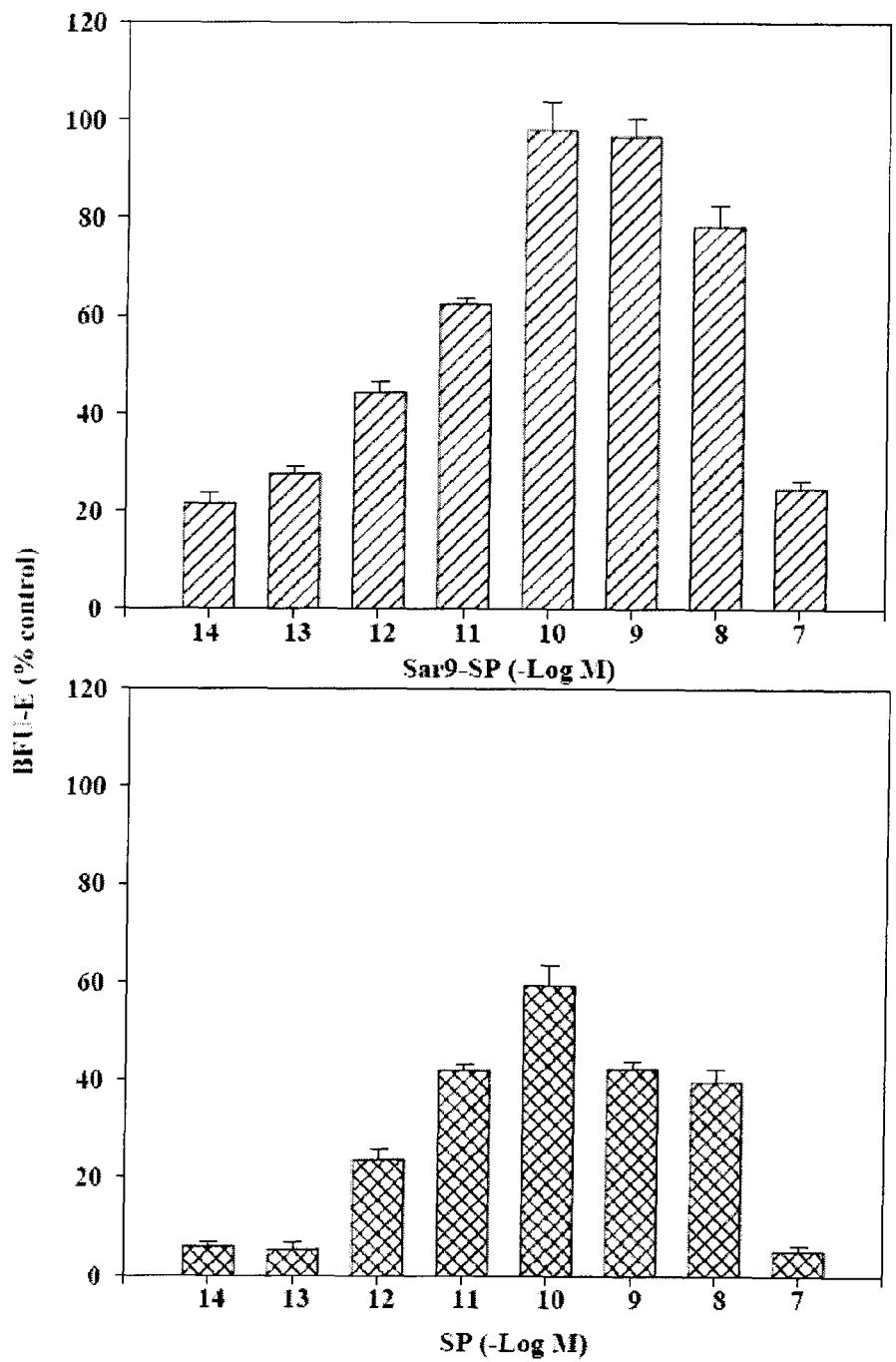

Fig. 2 Colony count of CFU-E vs. concentration for HOMSPERA® (Sar$^9$-SP) and substance P (SP).
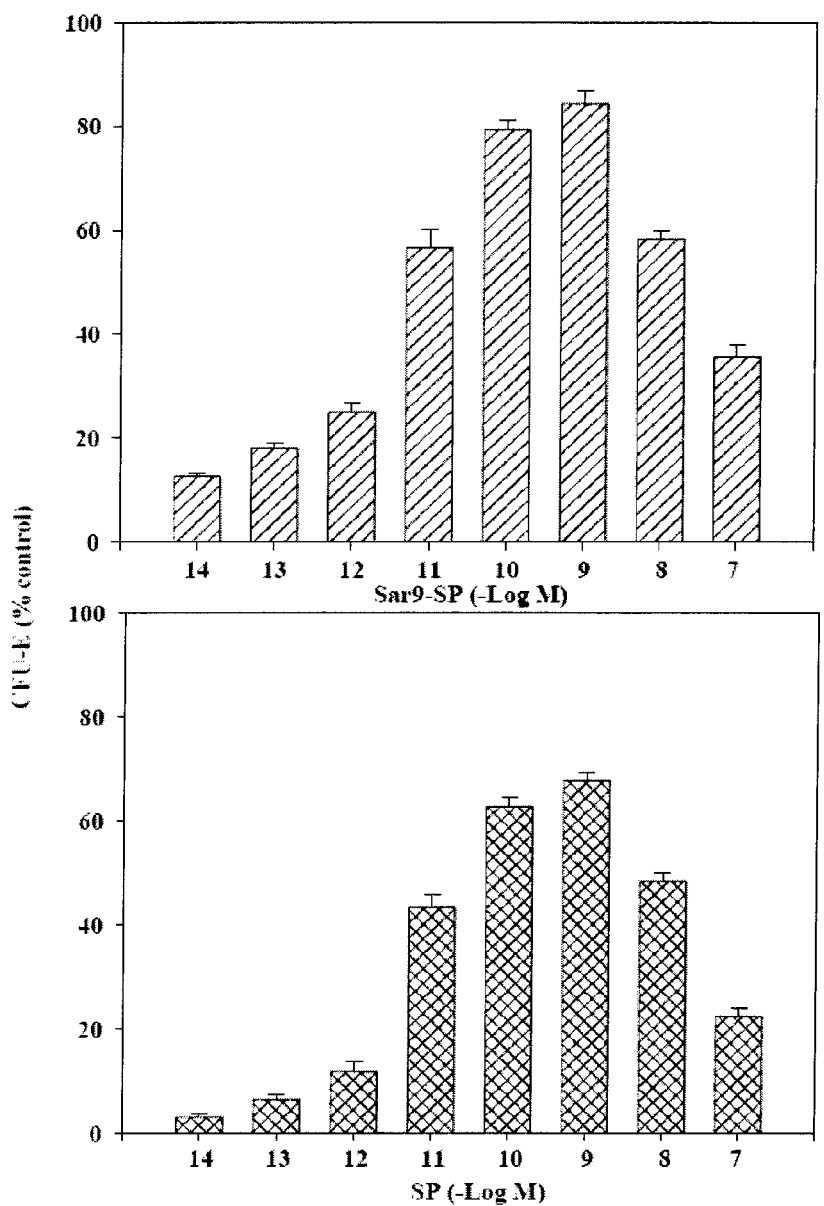

Fig. 3. Colony count of CFU-GM vs. concentration for HOMSPERA® (Sar$^9$-SP) and substance P (SP).
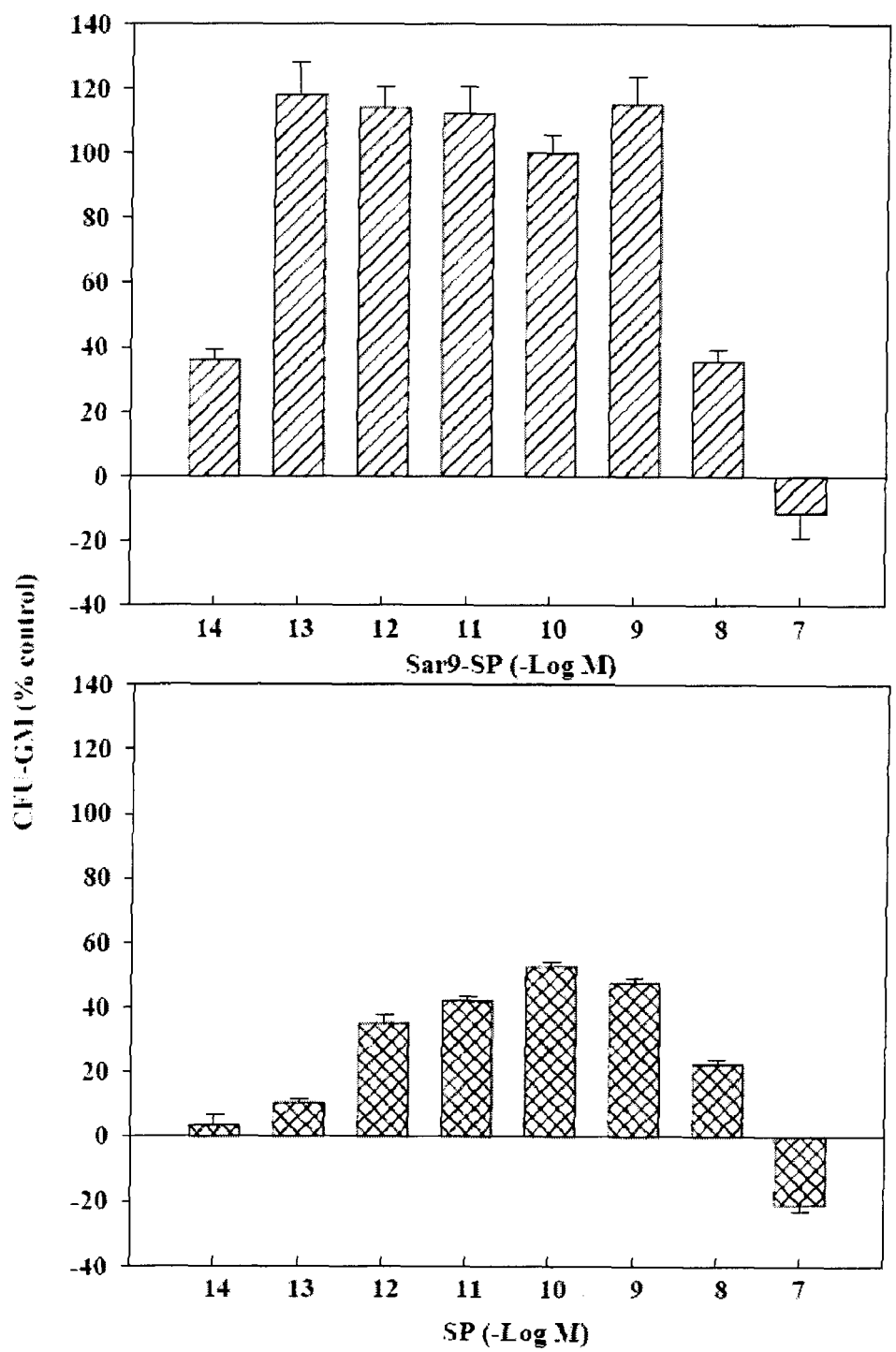

METHOD OF USING SUBSTANCE P ANALOGS FOR TREATMENT AMELIORATION OF MYELODYSPLASTIC SYNDROME

RELATED APPLICATION DATA

This application claims the benefit of Provisional Application No. 60/952,394, filed on Jul. 27, 2007, and Provisional Application No. 61/039,867, filed Mar. 27, 2008, under 35 U.S.C. §119(e).

1. FIELD OF THE INVENTION

The invention relates to the field of oncology. In particular, it relates to treatment, prevention or amelioration of myelodysplastic syndrome or preleukemia.

2. BACKGROUND OF THE INVENTION

Myelodysplastic syndrome (MDS) often presents as a refractory cytopenia in an older adult. The disorder can be asymptomic or patients may have fatigue, shortness of breath, loss of appetite, spontaneous bruising, petechia, bleeding of the gums or mucosal surfaces. Few therapies have been developed to treat MDS. Improvements are needed.

3. BRIEF SUMMARY OF THE INVENTION

The methods and compositions provide treatment or amelioration of myelodysplastic syndromes. In certain embodiments the methods and compositions provide treatment or amelioration of refractory anemia (RA), refractory anemia with ringed sideroblasts (RARS), refractory cytopenia with multilineage dysplasia (RCMD), refractory cytopenia with multilineage dysplasia and ringed sideroblasts (RCMD-RS), refractory anemia with excess blasts I and II, 5q syndrome or myelodysplasia unclassifiable.

4. DESCRIPTION OF THE FIGURES

FIG. 1 provides a graph showing a colony count of BFU-E vs. concentration for HOMSPERA® (Sar$^9$-SP) and substance P(SP).

FIG. 2 provides a graph showing a colony count of CFU-E vs. concentration for HOMSPERA® (Sar$^9$-SP) and substance P(SP).

FIG. 3 provides a graph showing a colony count of CFU-GM vs. concentration for HOMSPERA® (Sar$^9$-SP) and substance P(SP).

5. DETAILED DESCRIPTION OF THE INVENTION

At the outset of this detailed description, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "a polynucleotide" includes a plurality of polynucleotides, reference to "a substrate" includes a plurality of such substrates, reference to "a variant" includes a plurality of variants, and the like.

Terms such as "connected," "attached," "linked," and "conjugated" are used interchangeably herein and encompass direct as well as indirect connection, attachment, linkage or conjugation unless the context clearly dictates otherwise. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also encompassed. Where a combination is disclosed, each subcombination of the elements of that combination is also specifically disclosed and is within the scope of the embodiments. Conversely, where different elements or groups of elements are individually disclosed, combinations thereof are also disclosed. Where any element is disclosed as having a plurality of alternatives, examples in which each alternative is excluded singly or in any combination with the other alternatives are also hereby disclosed; more than one element can have such exclusions, and all combinations of elements having such exclusions are hereby disclosed.

Unless defined otherwise herein, all technical and scientific terms used herein have the same meaning as commonly understood by one of ordinary skill in the art to which this invention belongs. Although any methods and materials similar or equivalent to those described herein can be used in the practice or testing, the preferred methods and materials are described. Unless otherwise indicated, nucleic acids are written left to right in 5' to 3' orientation; amino acid sequences are written left to right in amino to carboxy orientation, respectively. The terms defined immediately below are more fully defined by reference to the specification as a whole.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

5.1 DEFINITIONS

The term "alkyl" refers to a saturated branched, straight chain or cyclic hydrocarbon radical. Typical alkyl groups include, but are not limited to, methyl, ethyl, propyl, isopropyl, butyl, isobutyl, t-butyl, pentyl, isopentyl, hexyl, and the like. In preferred embodiments, the alkyl groups are ($C_1$-$C_6$) alkyl.

The term "alkenyl" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, butenyl, isobutenyl, tert-butenyl, pentenyl, hexenyl and the like. In preferred embodiments, the alkenyl group is ($C_1$-$C_6$) alkenyl.

The term "alkynyl" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_1$-$C_6$) alkynyl.

The term "aryl" refers to an unsaturated cyclic hydrocarbon radical having a conjugated n electron system. Typical aryl groups include, but are not limited to, penta-2,4-diene, phenyl, naphthyl, anthracyl, azulenyl, chrysenyl, coronenyl, fluoranthenyl, indacenyl, idenyl, ovalenyl, perylenyl, phenalenyl, phenanthrenyl, picenyl, pleiadenyl, pyrenyl, pyranthrenyl, rubicenyl, and the like. In preferred embodiments, the aryl group is ($C_5$-$C_{20}$) aryl, with ($C_5$-$C_{10}$) being particularly preferred.

The term "alkaryl" refers to a straight-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthenobenzyl and the like. In preferred embodiments, the alkaryl group is ($C_6$-$C_{26}$) alkaryl, i.e., the alkyl, alkenyl or alkynyl moiety of the alkaryl group is ($C_1$-$C_6$) and the aryl moiety is ($C_5$-$C_{20}$). In particularly preferred embodiments, the alkaryl group is ($C_6$-$C_{13}$) alkaryl, i.e., the alkyl, alkenyl or alkynyl moiety of the alkaryl group is ($C_1$-$C_3$) and the aryl moiety is ($C_5$-$C_{10}$).

The term "alkheteroaryl" refers to a straight-chain alkyl, alkenyl or alkynyl group where one of the hydrogen atoms bonded to a terminal carbon atom is replaced with a heteroaryl moiety. In preferred embodiments, the alkheteroaryl group is 6-26 membered alkheteroaryl, i.e., the alkyl, alkenyl or alkynyl moiety of the alkheteroaryl is ($C_1$-$C_6$) and the heteroaryl is a 5-20-membered heteroaryl. In particularly preferred embodiments the alkheteroaryl is 6-13 membered alkheteroaryl, i.e., the alkyl, alkenyl or alkynyl moiety is a 5-10 membered heteroaryl.

The term "heteroaryl" refers to an aryl moiety wherein one or more carbon atoms is replaced with another atom, such as N, P, O, S, As, Se, Si or Te. Typical heteroaryl groups include, but are not limited to, acridarsine, acridine, arsanthridine, arsindole, arsindoline, carbazole, β-carboline, chromene, cinnoline, furan, imidazole, indazole, indole, indolizine, isoarsindole, isoarsinoline, isobenzofuran, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiophene and anthenes. In preferred embodiments, the heteroaryl group is a 5-20 membered heteroaryl, with 5-10 membered aryl being particularly preferred.

The term "myelodysplastic syndrome (MDS)" refers to disorders due to somatic mutation of hematopoietic precursors.

The term "substituted alkyl, alkenyl, alkynyl, aryl alkaryl, heteroaryl or alkheteroaryl" refers to an alkyl, alkenyl, alkynyl, aryl, alkaryl, heteroaryl or alkheteroaryl group in which one or more hydrogen atoms is replaced with another substituent. Preferred substituents include —OR, —SR, —NRR, —NO$_2$, —CN, halogen, —C(O)R, —C(O)OR and —C(O)NR, where each R is independently hydrogen, alkyl, alkenyl, alkynyl, aryl, alkaryl, heteroaryl or alkheteroaryl.

5.2 ABBREVIATIONS

HPP-SP is an abbreviation for High Proliferative Potential-Stem and Progenitor cell.

CFC-GEMM is an abbreviation for Colony Forming Cells-Granulocyte, Erythroid, Macrophage, Megakaryocyte.

GM-CFC is an abbreviation for Granulocyte-Macrophage-Colony Forming Cells.

Mk-CFC is an abbreviation for Megakaryocyte-Colony Forming Cells.

T-CFC is an abbrevition for T-lymphocyte-Colony Forming Cells.

B-CFC is an abbreviation for B-lymphocyte-Colony Forming Cells.

CFU-Mk is an abbreviation for Colony Forming Unit—Megakaryocyte.

BFU-E is an abbreviation for Blast Forming Unit—Erythroid.

CFU-E is an abbreviation for Colony Forming Unit—Erythroid.

CFU-GM is an abbreviation for Colony Forming Unit—Granulocyte/Macrophage.

5.3 METHODS

Myelodysplastic syndrome is a group of disorders, historically termed preleukemia, refractory anemias, Philadelphia chromosome—negative chronic myelocytic leukemia, chronic myelomonocytic leukemia, or agnogenic myeloid metaplasia, resulting from a somatic mutation of hematopoietic precursors. Etiology is often unknown, but risk is increased with exposure to chemotherapeutic agents, particularly long or intense regimens and those involving alkylating agents and epipodophyllotoxins The chromosomal abnormalities or disorders of refractory anemia (RA), refractory anemia with ringed sideroblasts (RARS), refractory cytopenia with multilineage dysplasia (RCMD), refractory cytopenia with multilineage dysplasia and ringed sideroblasts (RCMD-RS), refractory anemia with excess blasts I and II, 5q syndrome or myelodysplasia unclassifiable are dysplastic syndromes referred to collectively herein as myelodysplastic syndrome (MDS).

MDS is generally categorized by bone marrow findings. Refractory anemia generally is anemia with reticulocytopenia, normal or hypercellular marrow with erythroid hyperplasia and dyserythropoiesis and blasts of ≦5%. Refractory anemia with sideroblasts generally presents the same as refractory anemia with the added presence of ringed sideroblasts that are about >15% of nucleated marrow cells. Refractory anemia with excess blasts presents with some cytopenia with ≧2 cell lines with morphologic abnormalities of blood cells and hypercellular marrow with dyserythropoiesis and dysgranulopoiesis and blasts of about 5% to about 20% of nucleated marrow cells. Chronic myelomonocytic leukemia presents similarly to refractory anemia with excess blasts with absolute monocytosis in blood and significant increase in marrow monocyte precursors. Refractory anemia with excess blasts in transformation presents as refractory anemia with excess blasts and one or more of the following: ≧5% blasts in blood, 20-30% blasts in marrow and Auer rods in granulocyte precursors. Merck Manual, 18$^{th}$ edition, Merck Publishing.

Myelodysplastic syndromes are considered clonal stem cell diseases that are characterized by peripheral cytopenias in the setting of a normocellular or hypercellular bone marrow that morphologically shows bilineage or trilineage dysplasia. Mechanisms of disease include pluripotent stem cell damage, abnormalities in proliferation, differentiation, and apoptosis leading to an ineffective hematopoiesis. The most common diagnosis include refractory anemia (RA), refractory anemia with ringed sideroblast (RARS), refractory anemia with excess blast (RAEB), and refractory anemia with excess blast in transformation Refractory Anemia with Excess Blasts in Transition (RAEBt) usually transitions quickly to Acute Myeloid Leukemia (AML) and has the worst prognosis of any of the MDS subtypes, with average survival of 5 months. Patients have low blood counts, 20-30% of bone marrow cells are immature blasts, and blood may contain up to 5% blasts. Auer rods may be visible, consisting of fused lysosomes and lysosomal constituents. RAEBt MDS has a high propensity for transformation to myeloid leukemia but can also transform into acute leukemia of other hematopoietic lineage. Overlapping features of MDS with aplastic anemia, T-cell large granular lymphocyte lymphoproliferative disorder, and paroxysmal nocturnal hemoglobinuria suggest a shared pathophysiologic mechanism of marrow failure.

Stem cell transplantation is one therapy available. REVLIMID® (lenalidomide, Celgene Corp., Summit, N.J.) is currently approved drug for MDS. In one embodiment, the substance P analogs can be administered with lenalidomide.

Myelodysplastic syndrome (MDS) encompasses a collection of hematological disorders characterized by unsuccessful stem cell differentiation. Neumeister, et al., 2002 *Am. J. Cancer* 1(5): 301-11. MDS can affect the myeloid cell lineages including erythrocytic, granulocytic and megakaryocytic cell lines and cause anemia, neutropenia, and thrombocytopenia respectively. The depletion of effective blood cells can be, in part, from exposures to chemotherapy, radiation, viral infections, chemical genotoxins, or from genetic predisposition. Often, conditions can progress to leukemia—more specifically, acute myeloid leukemia (AML). MDS and associated disorders like leukemia that cause myelosuppression can be counteracted upon treatment with substance P analogs. The treatment may be therapeutic or prophylactic.

Substance P has been shown to induce the production of hematopoietic growth factors. Rameshwar, et al., 1993, *Blood*, 81(2): 391-398. However, Applicants have surprisingly discovered that certain substance P analogs can induce proliferation and differentiation of hematopoietic cells to a greater extent than native substance P. Furthermore, the hematopoietic effects of certain substance P analogs can be achieved at concentrations much lower than native substance P.

The substance P analogs are believed particularly useful for the treatment of RAEBt MDS. Without intending to be bound to any particular theory or mechanism of action, the substance P analogs, as shown in the examples below, exhibit GM-CSF-like activity in that the substance P analogs can promote differentiation of hematopoietic stem cells, especially for example HPP-SP and GM-CFC lineages into granulocyte macrophage precursors, which can lead to increased circulating granulocyte and macrophage levels. See, e.g., Example 4. GM-CSF has been shown to increase neutrophils and inhibit the infection rate in RAEB-t patients. See, Economopoulos T. et al., 1996, *Leukemia Res.* 20:385. Accordingly, in certain aspects, provided herein are methods for treating, preventing, or ameliorating a symptom of RAEBt MDS, comprising administering a substance P analog as described herein to a subject in need thereof. In certain embodiments, the symptom is selected from fatigue, increased tendency to bruise easily, unusually large bruises, nose or gum bleeding, unexpected bleeding, unusual colored spotting under skin, prolonged bleeding, reddish urine, black or bloody stool, body chills, coughing, wheezing, shortness of breath, skin that is paler than normal, fevers, dizziness, lightheadedness, a tendency to feel cold, difficulty concentrating or thinking clearly, diarrhea, painful or difficult urination, cloudy urine, reddish or swelling skin, excessive sweating, and frequent infections, e.g., sore throat, ear infection, mouth ulcer or gum infection.

The methods can be used to increase the numbers of any blood cell class or subclass. These include erythrocytes, leukocytes, and platelets. It further includes neutrophils, band cells, T lymphocytes, B lymphocytes, monocytes, eosinophils, and basophils. More particularly, these include T helper cells, CD45 positive cells, antigen presenting cells, CD4 positive cells, CD8 positive cells, and T cells expressing Toll Like Receptor (TLR) types.

In certain embodiments, the methods can be used to increase differentiation of cell populations selected from HPP-SP, GM-CFC, CFC-GEMM and B-CFC progenitor cells. In certain embodiments, the methods can be used to increase differentiation of cell populations selected from HPP-SP, GM-CFC, T-CFC, Mk-CFC, CFC-GEMM and B-CFC progenitor cells. In certain embodiments, the methods can be used to increase differentiation of cell populations selected from BFU-E, CFU-E, CFU-GM and CFU-Mk cell progenitor cells.

In certain embodiments, the methods can be used to increase proliferation of cell populations selected from HPP-SP, GM-CFC, T-CFC, Mk-CFC, CFC-GEMM and B-CFC progenitor cells. In certain embodiments, the methods can be used to increase proliferation of cell populations selected from B-CFC and T-CFC cells. In certain embodiments, the methods can be used to increase proliferation of cell populations selected from BFU-E, CFU-E, CFU-GM and CFU-Mk cells.

The HPP-SP population comprises stem and progenitor cells that can express CD90+/CD133+/CD34+ markers. The BFU-E population comprises erythroid cells that can express CD38+/Glycophorin-A+ markers. The GM-CFC population comprises granulocyte-macrophage colony forming cells that can express CD38+/CD14+/CD15+ markers. The Mk-CFC population comprises megakaryocyte colony forming cells that can express CD41+/CD61+ markers. The T-CFC population comprises T-lymphocyte colony forming cells that can express CD3+/CD4+/CD8+ cell markers. The B-CFC population comprises B-lymphocyte colony forming cells that can express CD19+ markers. The CFC-GEMM population comprises granulocyte, erythroid, macrophage and megakaryocyte cells. Cells of the CFC-GEMM population can express cell markers for their particular lineage as well as CD34+ and CD133+ (e.g., granulocytes can express CD38+/CD14+/CD15+ as well as CD34+ and CD133+ markers, erythroid cells can express CD38+/Glycophorin-A+ markers as well as CD34+ and CD133+ markers).

Determining counts of blood cell types, classes, subclasses and subtypes can be done according to any method known in the art. Many such methods are automated and are provided in a standard complete blood count. Parameters of the blood which can be determined and used for monitoring include red blood cell count, white blood cell count, platelet count, hemoglobin concentration, hematocrit, MCV, red blood cell size, count of any blood cell type or subtype, etc. The determining of counts or other blood parameters can be performed before and/or after treatment and can be performed multiple times for continued monitoring.

Myeloproliferative disorders can be treated or ameliorated by the administration of an effective amount of a substance P analog to a human in need thereof wherein the substance P analog is of Formula (I):

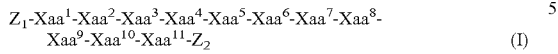

$$Z_1\text{-}Xaa^1\text{-}Xaa^2\text{-}Xaa^3\text{-}Xaa^4\text{-}Xaa^5\text{-}Xaa^6\text{-}Xaa^7\text{-}Xaa^8\text{-}Xaa^9\text{-}Xaa^{10}\text{-}Xaa^{11}\text{-}Z_2 \qquad (I)$$

or a pharmaceutically acceptable salt thereof, wherein:

$Xaa^1$ is Arg, Lys, 6-N methyllysine or (6-N, 6-N) dimethyllysine;

$Xaa^2$ is Pro or Ala;

$Xaa^3$ is Lys, Arg, 6-N-methyllysine or (6-N, 6-N) dimethyllysine;

$Xaa^4$ is Pro or Ala;

$Xaa^5$ is Gln or Asn;

$Xaa^6$ is Gln or Asn;

$Xaa^7$ is Tyr, Phe, or Phe substituted with chlorine at position 2, 3 or 4;

$Xaa^8$ is Tyr, Phe, or Phe substituted with chlorine at position 2, 3 or 4;

$Xaa^9$ is Gly, Pro, Ala or N-methylglycine;

$Xaa^{10}$ is Leu, Val, Ile, Norleucine, Met, Met sulfoxide, Met sulfone, N-methylleucine, or N-methylvaline;

$Xaa^{11}$ is Met, Met sulfoxide, Met sulfone, or Norleucine;

$Z_1$ is $R_2N$— or $R^C(O)NR$—;

$Z_2$ is —$C(O)NR_2$ or —$C(O)OR$ or a salt thereof;

each R is independently R is —H, $(C_1\text{-}C_6)$ alkyl, $(C_1\text{-}C_6)$ alkenyl, $(C_1\text{-}C_6)$ alkynyl, $(C_5\text{-}C_{20})$ aryl, $(C_6\text{-}C_{26})$ alkaryl, 5-20 membered heteroaryl or 6-26 membered alkheteroaryl; and each "−" between residues $Xaa^1$ through $Xaa^{11}$ independently designates an amide linkage, a substitute amide linkage or an isostere of an amide. In certain embodiments the substance P analogs can be of Formula (I) with the proviso that the substance P analog is not substance P. In certain embodiments, the substance P analog can be in a salt, e.g., associated with a cation or anion, form. Any pharmaceutically acceptable salt known to one skilled in the art can be used in the salt forms of the substance P analogs.

In one embodiment, the substance P analog can be of Formula (I) as described herein wherein $Xaa^1$ is Arg; $Xaa^2$ is Pro; $Xaa^3$ is Lys; $Xaa^4$ is Pro; $Xaa^5$ is Gln; $Xaa^6$ is Gln; $Xaa^7$ is Tyr, Phe, or Phe substituted with chlorine at position 4; $Xaa^8$ is Tyr, Phe, or Phe substituted with chlorine at position 4; $Xaa^9$ is Gly, Pro or N-methylglycine; $Xaa^{10}$ is Leu; and $Xaa^{11}$ is Met, Met sulfoxide, Met sulfone or Norleucine.

In a preferred embodiment, the substance P analog can be of Formula (I) as described herein wherein the "−" between residues $Xaa^1$ through $Xaa^{11}$ designates $C(O)NH$—; $Z_1$ is $H_2N$—; and $Z_2$ is —$C(O)NH_2$.

In another preferred embodiment, the substance P analog can be:

| | |
|---|---|
| RPKPQQFFGLM; | (SEQ ID NO.: 1) |
| RPKPQQFFGLNle; | (SEQ ID NO.: 2) |
| RPKPQQFFPLM; | (SEQ ID NO.: 3) |
| RPKPQQFFMeGlyLM; | (SEQ ID NO.: 4) |
| RPKPQQFTGLM; | (SEQ ID NO.: 5) |
| RPKPQQF(4-Cl)F(4-Cl)GLM; | (SEQ ID NO.: 6) |
| RPKPQQFFGLM(O); | (SEQ ID NO.: 7) |
| RPKPQQFFMeGlyLM(O); | (SEQ ID NO.: 8) |
| RPKPQQFFGLM(O$_2$); and | (SEQ ID NO.: 9) |
| RPKPQQFFMeGlyLM(O$_2$). | (SEQ ID NO.: 10) |

In another preferred embodiment, the substance P analog can be:

| | |
|---|---|
| RPKPQQFFGLNle; | (SEQ ID NO.: 2) |
| RPKPQQFFPLM; | (SEQ ID NO.: 3) |
| RPKPQQFFMeGlyLM; | (SEQ ID NO.: 4) |
| RPKPQQFTGLM; | (SEQ ID NO.: 5) |
| RPKPQQF(4-Cl)F(4-Cl)GLM; | (SEQ ID NO.: 6) |
| RPKPQQFFGLM(O); | (SEQ ID NO.: 7) |
| RPKPQQFFMeGlyLM(O); | (SEQ ID NO.: 8) |
| RPKPQQFFGLM(O$_2$); and | (SEQ ID NO.: 9) |
| RPKPQQFFMeGlyLM(O$_2$). | (SEQ ID NO.: 10) |

In an even more preferred embodiment, the substance P analog can be $Z_1$-RPKPQQFFMeGlyLM(O$_2$)-$Z_2$; wherein $Z_1$ is $NH_2$ and $Z_2$ is $C(O)NH_2$. In one embodiment, the substance P analog is not substance P (SEQ ID NO 1).

As will be understood by those of skill in the art, substance P (SEQ ID NO 1) refers to peptide: Arg Pro Lys Pro Gln Gln Phe Phe Gly Leu Met, or the single letter representation RPKPQQFFGLM (SEQ ID NO 1). As such, a substance P analog as used in the methods and compositions described herein refers to a substance P analog that comprises one or more amino acids substitutions relative to SEQ ID NO 1 and can either compete with substance P for binding to its receptor (NK-1) or agonize the NK-1 (neurokinin) receptor according to an assay conventional to the art, e.g., as described in Shue, et al., *Bioorgan Med Chem Letters* 2006, 16(4): 1065-1069. The amino acid substitutions can be conservative or non-conservative substitutions. Further, the amino acid substitutions can include substitutions of non-standard amino acids (e.g., amino acids other than the 20 amino acids normally encoded by the genetic code). In one example, the substance P analog can comprise norleucine (Nle). In yet another example, the substance P analog can comprise sarcosine (Sar) or N-methylglycine (MeGly). In yet another example, the substance P analog can comprise phenylalanine that is substituted with between 1 and 4 chlorines, more preferably 1 chlorine.

In one embodiment the methionine residue side chain sulfur (S) can be oxidated. In one embodiment the methionine is methionine sulfoxide (—NH—CH(CO)—CH$_2$—CH$_2$—S(O)CH$_3$). In one embodiment the methionine is methionine sulfone or methionine S, S, dioxide, (—NH—CH(CO)—CH$_2$—CH$_2$—S(O$_2$)CH$_3$), also referred to herein as Met(O)$_2$.

In one embodiment, the substance P analog is [Nle$^{11}$]-substance P, e.g., the substance P analog wherein the 11$^{th}$ amino acid position is norleucine, i.e., the peptide: Arg Pro Lys Pro Gln Gln Phe Phe Gly Leu Nle (RPKPQQFFGLNle) (SEQ ID NO.:2). In one embodiment, the substance P analog is [Pro$^9$]-substance P, which refers to the substance P analog wherein the 9$^{th}$ amino acid position is proline and has the sequence: Arg Pro Lys Pro Gln Gln Phe Phe Pro Leu Met (RPKPQQFFPLM) (SEQ ID NO.:3). In one embodiment, the substance P analog is [Sar$^9$]-substance P, which refers to the substance P analog wherein the 9$^{th}$ amino acid position is Sarcosine or N-Methylglycine and has the sequence: Arg Pro Lys Pro Gln Gln Phe Phe MeGly Leu Met (RPKPQQFFMeG-lyLM) (SEQ ID NO.:4). In one embodiment, the substance P analog is [Tyr$^8$]-substance P refers to the substance P analog wherein the 8$^{th}$ amino acid position is tyrosine and has the sequence: Arg Pro Lys Pro Gln Gln Phe Tyr Gly Leu Met (RPKPQQFTGLM) (SEQ ID NO 5). [p-Cl-Phe$^{7,8}$]-substance P refers to the substance P analog wherein the Phenylalanine residue at positions 7 and 8 are chlorinated at the 4 position and has the sequence: Arg Pro Lys Pro Gln Gln Phe(4-Cl) Phe(4-Cl) Gly Leu Met-NH$_2$ (RPKPQQF(4-CL)F(4-CL)GLM) (SEQ ID NO.:6). In one embodiment, the 11$^{th}$ amino acid residue is Methionine sulfoxide, RPKPQQFF-GLM(O) (SEQ ID NO:7). In one embodiment, the 9$^{th}$ amino acid residue is Sarcosine and the 11$^{th}$ residue is Methionine sulfoxide, RPKPQQFFMeGlyLM(0) (SEQ ID NO:8). In one embodiment, the 11$^{th}$ amino acid residue is Methionine sulfone, RPKPQQFFGLM(O)$_2$ (SEQ ID NO:9). [Sar$^9$, Met(O$_2$)$^{11}$]-substance P refers to the substance P analog wherein the 9$^{th}$ amino acid position is Sarcosine or N-Methylglycine and the 11$^{th}$ amino acid position is Met(O$_2$) and has the sequence: Arg Pro Lys Pro Gln Gln Phe Phe MeGly Leu Met-O$_2$ (RPKPQQFFMeGlyLM-O$_2$) (SEQ ID NO.:10).

It will be apparent to one skilled in the art that the amino (designated herein as Z$_1$) or carboxy terminus (designated herein as Z$_2$) of the substance P analogs can be modified. Specifically contemplated for use in the methods and compositions are "blocked" forms of the substance P analogs, i.e., forms of the substance P analogs in which the N- and/or C-terminus is blocked with a moiety capable of reacting with the N-terminal —NH$_2$ or C-terminal —C(O)OH. In some embodiments the N- and/or C-terminal charges of the substance P analogs can be an N-acylated peptide amide, ester, hydrazide, alcohol and substitutions thereof. In a preferred embodiment, either the N- and/or C-terminus (preferably both termini) of the substance P analogs are blocked. Typical N-terminal blocking groups include RC(O)—, where R is —H, (C$_1$-C$_6$) alkyl, (C$_1$-C$_6$) alkenyl, (C$_1$-C$_6$) alkynyl, (C$_5$-C$_{20}$) aryl, (C$_6$-C$_{26}$) alkaryl, 5-20 membered heteroaryl or 6-26 membered alkheteroaryl. Preferred N-terminal blocking groups include acetyl, formyl and dansyl. Typical C-terminal blocking groups include —C(O)NRR and —C(O)OR, where each R is independently defined as above. Preferred C-terminal blocking groups include those wherein each R is independently methyl. In another preferred embodiment the C-terminal group is amidated.

Substituted amides generally include, but are not limited to, groups of the formula —C(O)NR—, wherein R is (C$_1$-C$_6$) alkyl, substituted (C$_1$-C$_6$) alkyl, (C$_1$-C$_6$) alkenyl, substituted (C$_1$-C$_6$) alkenyl, (C$_1$-C$_6$) alkynyl, substituted (C$_1$-C$_6$) alkynyl, (C$_5$-C$_{20}$) aryl, substituted (C$_5$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl and substituted 6-26 membered alkheteroaryl.

Amide isosteres generally include, but are not limited to, —CH$_2$NH—, —CH$_2$S—, —CH$_2$CH$_2$—, —CH=CH— (cis and trans), —C(O)CH$_2$—, —CH(OH)CH$_2$— and —CH$_2$SO—. Compounds having such non-amide linkages and methods for preparing such compounds are well-known in the art (see, e.g., Spatola, March 1983, Vega Data Vol. 1, Issue 3; Spatola, 1983, "Peptide Backbone Modifications" In: Chemistry and Biochemistry of Amino Acids Peptides and Proteins, Weinstein, ed., Marcel Dekker, New York, p. 267 (general review); Morley, 1980, Trends Pharm. Sci. 1:463-468; Hudson et al., 1979, Int. J. Prot. Res. 14:177-185 (—CH$_2$NH—, —CH$_2$CH$_2$—); Spatola et al., 1986, Life Sci. 38:1243-1249 (—CH$_2$—S); Hann, 1982, J. Chem. Soc. Perkin Trans. I. 1:307-314 (—CH=CH—, cis and trans); Almquist et al., 1980, J. Med. Chem. 23:1392-1398 (—COCH$_2$—); Jennings-White et al., Tetrahedron. Lett. 23:2533 (—COCH$_2$—); European Patent Application EP 45665 (1982) CA 97:39405 (—CH(OH)CH$_2$—); Holladay et al., 1983, Tetrahedron Lett. 24:4401-4404 (—C(OH)CH$_2$—); and Hruby, 1982, Life Sci. 31:189-199 (—CH$_2$—S—).

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3039-3049.

5.4 COMPOSITIONS AND KITS

In one embodiment, provided herein are compositions for administration of a substance P analog to prevent, treat, or ameliorate myelodysplastic syndrome. In one embodiment, provided herein is a composition comprising an effective amount of a substance P analog, for example, a substance P analog according to Formula (I) as described herein.

In one embodiment, the composition is a pharmaceutical composition. In a preferred embodiment, the composition can be a pharmaceutical composition of [Sar$^9$, Met(O$_2$)$^{11}$]-substance P (SEQ ID NO.:10). In one embodiment, the composition can be a pharmaceutical composition of RPK-PQQFFMeGlyLM(O$_2$)—NH$_2$, carboxy-terminally amidated [Sar$^9$, Met(O$_2$)$^{11}$]-substance P (SEQ ID NO.:10). In one embodiment, an effective amount of a substance P analog is an amount sufficient to reduce or diminish the signs or symptoms of MDS.

Pharmaceutical compositions of the substance P analogs comprise a therapeutically effective amount of a compound described herein, formulated together with one or more pharmaceutically acceptable carriers. As used herein, the term "pharmaceutically acceptable carrier" or "carrier" refers to a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar, buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Injectable parenteral preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid can be used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution that, in turn, can depend upon crystal size and crystalline form. Alternatively, delayed absorption of a parenterally administered drug form can be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides).

Depot injectable formulations can also be prepared by entrapping the drug in liposomes or microemulsions that are compatible with body tissues.

In preferred embodiments, the parenteral composition can be administered intravenously, intramuscularly, subcutaneously or intradermally.

Intravenous, aerosol inhalation, topical, intratracheal, intrabronchial, intranasal, subcutaneous, sublingual, and oral administrations can be used. Suitable concentration ranges of substance P or its bioactive analog in an aerosol administered is between about 0.1 µM and about 5000 mM, Exemplary concentrations which can be used include about 1 mM, about 10 mM, about 50 mM, about 75 mM, about 100 mM, about 300 mM and about 1000 mM. For intramuscular injections, a volume of about 0.1 to 1.0 ml/kg of body weight can be used.

One skilled in the art can routinely determine dosages of substance P analogs for use in the methods and compositions described herein according to conventional parameters such as, for example, mass, distribution and clearance rates, etc. Doses will generally be from about 0.5 ng/kg to about 500 mg/kg.

Solid dosage forms for oral administration include capsules, tablets, pills, powders, and granules. In such solid dosage forms, the active compound can be mixed with at least one inert, pharmaceutically acceptable excipient or carrier such as sodium citrate or dicalcium-phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid compositions of a similar type can also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Absorption through the gastrointestinal tract can be accomplished with peptides particularly if formulated in an appropriate composition. For example, peptides, such as the substance P analogs can be made in a pro-drug composition to provide oral absorption. See, Borchardt 1999, *J. Controlled Release* 62(1-2): 231-238, Catnach et al., 1994, *Gut* 35(4): 441-444. In another embodiment, the oral routes of administration (including but not limited to ingestion, buccal and sublingual routes) can be used. In preferred embodiments, appropriate formulations (e.g., enteric coatings) are used to avoid or minimize degradation of the active ingredient, e.g., in the harsh environments of the oral mucosa, stomach and/or small intestine. Oral pharmaceutical compositions of the substance P analog peptide can be conjugated with NOBEX™. (Protein Delivery Inc.) polymers as described in U.S. Pat. Nos. 5,359,030; 5,438,040; 5,681,811; 6,191,105; 6,309,633 and 6,380,405, incorporated herein by reference.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Compositions for rectal or vaginal administration are preferably suppositories that can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or transdermal administration of a compound can include ointments, pastes, creams, lotions, gels, powders, solutions, sprays, inhalants or patches. The active component can be admixed under sterile conditions with a pharmaceutically acceptable carrier and any needed preservatives or buffers as may be required. Ophthalmic formulations, ear drops, and the like are also contemplated as being within the scope of these embodiments.

The ointments, pastes, creams and gels can contain, in addition to one or more substance P analogs, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compounds and compositions can also be formulated for use as topical powders and sprays that can contain excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutical compositions can also be formulated for delivery as a liquid aerosol or inhalable dry powder. Liquid aerosol formulations can be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations can be delivered using an aerosol forming device, such as a jet, vibrating porous plate or ultrasonic nebulizer, preferably selected to allow the formation of aerosol particles having with a mass medium average diameter predominantly between 1 to 5 µm. Further, the formulation preferably has balanced osmolarity ionic strength and chloride concentration, and the smallest aerosolizable volume able to deliver effective dose of the compounds to the site of the delivery. Additionally, the aerosolized formulation preferably does not impair negatively the functionality of the airways and does not cause undesirable side effects.

Aerosolization devices suitable for administration of aerosol formulations, for example, jet, vibrating porous plate, ultrasonic nebulizers and energized dry powder inhalers, that are able to nebulize the formulation into aerosol particle size predominantly in the size range from 1-5 µm. Predominantly means that at least 70% but preferably more than 90% of all generated aerosol particles are 1 to 5 µm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and UltraAire7 (Omron Healthcare, Inc., Vernon Hills, Ill.) ultrasonic nebulizers.

The substance P analogs can be advantageously administered as a liquid dosage form at a concentration between about 0.1 µM and 1M. More preferably from abut 0.1 mM to about 100 mM. In an even more preferred embodiment, the substance P analogs can be administered based on the subject's weight. In one embodiment, the substance P analog is administered at a dose of about 0.01 mg/kg to about 10 mg/kg. In a more preferred embodiment, the compositions are administered at a dose of about 0.05 mg/kg to about 5 mg/kg. Other exemplary dosage forms include about 1 mL of about 100 mM substance P analog solution, about 1 mL of about 1 mM substance P analog solution or about 1 mL of about 10 µM substance P analog solution administered parenterally or by inhalation.

Methods of formulation are well known in the art and are disclosed, for example, in *Remington*: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art. It will be appreciated that the preferred route of administration and thus the type of pharmaceutical composition can vary with the condition, age and compliance of the recipient.

The methods and compositions can be administered in a frequency and duration for prevention or amelioration of decreased blood cells due to drugs or therapeutic radiation.

In one embodiment, the compositions can be administered one time (e.g. single dose). In one embodiment, the compositions can be administered multiple times, for example concomitantly with a medicament or following a medication regimen, for example. In one embodiment, the composition can be given hours, days, weeks or even months after a medicinal or therapeutic regimen (i.e. chemotherapy or radiation therapy). In one embodiment, the compositions can be administered intermittently, for example, every 3 days, every 7 days, every 14 days, every 30 days, every 60 days, every 90 days, every 180 days, every 360 days and the like.

In one embodiment provided herein are a kit for administering a substance P analog and a drug (e.g. an immunomodulatory drug (IMID™, Celgene) or a biological response modifier). For example, such a kit can comprise both an anti-cancer drug and at least one substance P analog and optionally, one or more biological response modifier. In certain embodiments, the substance P analog can be of Formula I as described herein. The drug and substance P analog can be in separate, or divided or undivided containers. The two agents can be in liquid, dried, lyophilized, or frozen form, as is convenient for the end user and good for shelf life. The treatments can be administered at one time or sequentially, over a period of, for example, one day, one week, one month, six months or twelve months.

6. EXAMPLES

6.1 Example 1

Preliminary Analysis of Effects of a Substance P Analog Following Lethal Radiation of Mice One purpose of the study is to determine the effects of HOMSPERA® (formerly RADILEX™; [Sar 9, Met (O$_2$) 11] Substance P) after exposure to a lethal dose of 60 Co radiation exposure. Another purpose of the study is to determine if intra-muscular injections of RADILEX™ can be as effective as aerosol inhalation of RADILEX™ at 8Gy 60 Co radiation level.

Blood draws (2 animals per group rotating every 5 days) for erythrocytes, leukocytes and platelets were taken to assess anemia, neutropenia and thrombocytopenia. Counts of erythrocytes, leukocytes and platelets were taken to assess anemia, neutropenia and thrombocytopenia and act as indicators of bone marrow damage and/or immune system destruction.

The mice received HOMSPERA® treatment within 2 hours of radiation exposure. The HOMSPERA® dosage was administered in a volume of 0.01 ml in a daily single treatment via IM injection into the hind limb muscle a single time, for the duration of the study (30 days), or until death.

The following regimens were tested on groups of 9-11 mice:
- 10 mM HOMSPERA® single intramuscular treatment
- 1 mM HOMSPERA® single intramuscular treatment
- 1 mM HOMSPERA® daily intramuscular treatment
- 75 uM HOMSPERA® single intramuscular treatment
- 75 uM HOMSPERA® daily intramuscular treatment
- 10 uM HOMSPERA® daily via nebulizer
- 50 uM HOMSPERA® daily via nebulizer
- 75 uM HOMSPERA® daily via nebulizer
- 100 uM HOMSPERA® daily via nebulizer
- 200 uM HOMSPERA® single administration via nebulizer at 2 hours post radiation exposure
- 1 mM HOMSPERA® single administration via nebulizer at 2 hours post radiation exposure
- 10 mM HOMSPERA® single administration via nebulizer at 2 hours post radiation exposure Radioprotective effects of HOMSPERA® were confirmed as the effects of lethal exposure were reversed. In particular, neutropenia and anemia were reversed in surviving animals. The normal white cell count for C57BL/6J mice is 6.2+2.7 K/microliter for males, 5.9+1.1 for females. Normal hematocrit is 45.4+1.7% for males, 46.2+1.2% for females. The mice that did not survive the highest radiation dose, 8 Gy, had white cell counts 1/10 of normal or less, and hematocrits of less than half normal. Mice that did survive had, on average, white cell counts at 1/10 of normal or higher, and hematocrits at half normal or higher. It is clear, although not statistically significant because of small sample size per group, that more mice administered HOMSPERA® survived the 8 Gy dose than would be expected to have survived, suggesting efficacy of HOMSPERA® treatment. In view of these promising results, further experiments described in the examples that follow were performed.

6.2 Example 2

Half-Life of Plasma HOMSPERA® Relative to Native Substance P

The objective was to determine the half-life of HOMSPERA® (RPKPQQFFMeGlyLM(O$_2$)—NH$_2$ (SEQ. ID. NO:10)) in plasma from three animal species.

Frozen plasma from mice, human and non-human primates (designated hereinafter as primates for simplicity) was obtained from Biochemed (Winchester, Va.) (human: Lot BC061107-07, primate: Lot CYNBREC-27070, mouse: Lot S-74242). EDTA was added as an anticoagulant during isolation of the plasma for all samples.

The plasma was thawed and 990 µL was added to a 1.5 mL microcentrifuge vial. To have a final concentration of HOMSPERA® in the plasma, two different stock solutions at either 1 mg/mL or 10 mg/mL were prepared using phosphate buffered saline (PBS), pH 7.4 at a 1× concentration. Ten µL of a 1 mg/mL solution were added to 990 µL of plasma for a final HOMSPERA® concentration of 7 µM and samples were vortexed to mix. Ten µL of a 10 mg/mL solution were added to 990 µL of plasma for a final HOMSPERA® concentration of 70 µM and samples were vortexed to mix. In a 96-deep-well plate, 50 µL of either the 7 µM or the 70 µM plasma samples were mixed with 50 µL of a 1×PBS, pH 7.4 solution.

For the preliminary half-life assessment, the 96-well plate was placed in a 37° C. oven for 0, 3, 10, 60, 120, and 180 min. Each sample per time point was terminated with the addition of 400 µL of 450 ng/mL glyburide in 90% acetonitrile (ACN) and 0.1% formic acid in water. Each sample was tested in duplicate. The plate was centrifuged at 4,000 rpm for 10 minutes and the supernatant was transferred to another 96-well plate. The supernatants were stored at −80° C. while other time points were being collected. Samples were evaporated using a TURBOVAP® and then reconstituted with 50 µL of 10 µg/mL of Pro$^9$-substance P (SEQ. ID. NO:3) in 40% acetonitrile and 0.1% formic acid in water. Pro$^9$-substance P functioned as an internal standard. Once the preliminary assessment was completed (data not shown), the time points were refined for the definitive portion. The time points assessed for the definitive study were 0, 10, 20, 30, 60, and 120 minutes. Samples were analyzed and quantitated by liquid chromatography/mass spectrometry (LC/MS).

The MS instrument was manufactured by Applied Biosystems (model: API 4000) and the LC portion of the instrument included a high pressure liquid chromatography (HPLC) pump made by Shimadzu (part number: LC-10ADvp) and an Agilent Poroshell HPLC column (part number: 300 SB-C18 (2.1×75 mm). The system solvent consisted of two different mobile phases, designated as A or B, to resolve HOMSPERA®. Mobile phase A was 95% H$_2$O, 5% ACN and 0.1% formic acid, and mobile phase B was 90% ACN, 10% H$_2$O, and 0.1% formic acid. The program used for separation on the HPLC column was a linear gradient from 0 to 1.5 minutes going from 0% B to 50% B, and from 50% B to 90% B at 1.5 minutes to 1.6 minutes, a hold at 90% B from 1.6 minutes to 2 minutes followed by a gradient from 90% B to 0% B until 2.1 minutes and a hold at 0% B from 2.1 to 2.5 minutes. The LC/MS was programmed to operate using a flow rate of 0.6 mL/min and 5 µL of sample were injected onto the HPLC column for each run. Additionally, the instrument was equipped with a turbo ion spray source, which was set to operate in the positive ion interface and multiple reaction monitoring acquisition modes. The source temperature was 500° C. and the total run time was 2.5 minutes. The parent/daughter ion pair of HOMSPERA® was 698.8/348.4 and was 695.2/211.3 for the internal standard, Pro$^9$-substance P.

At the lower concentration, 7 μM, the mean half-life in mice was 33 minutes (st. dev. 3). The mean half-life for humans and primates at 7 μM was very similar with a mean half-life in primates of 37 minutes (st. dev. 4). At higher concentrations, 70 μM, the mean mouse half-life was 38 minutes. (st. dev. 1). The mean half-life for primates at 70 μM was 59 minutes (st. dev. 6) and 66 minutes for humans (st. dev. 0). Without being bound to any theory, it is proposed that the higher concentration of HOMSPERA® saturated the ex vivo system perhaps by binding to other proteins in the plasma that would stabilize or protect HOMSPERA® from enzymatic degradation. Accordingly, it is concluded the half-life of HOMSPERA® is between 30-60 minutes for the three species examined.

TABLE 1

Ex Vivo HOMSPERA ® Half-Life in Plasma in Three Animal Species.

| Species | 7 μM | | 70 μM | |
|---|---|---|---|---|
| | Mean | St. dev. | Mean | St. dev |
| Mouse | 33 | 3 | 38 | 1 |
| Primate | 37 | 4 | 59 | 6 |
| Human | 35 | 4 | 66 | 0 |

With regard to substance P, Berger et al., reported that native substance P is rapidly degraded in rat brain fractions and in human plasma ex vivo. Berger et al., 1979, *Biochem. Pharmacol.* 28: 3173-3180. At concentrations below $10^{-7}$M, the native peptide had a half-life of 9.3 minutes when incubated in a 1 mg/mL rat brain homogenate fraction. The half-life of the native peptide in plasma, ex vivo, was 24 minutes.

Blumberg and Teichberg determined native substance P has a half-life of about 5 minutes (±2 min) when 0.2 μM was incubated in 1 mg/mL rat brain homogenate. Blumberg and Teichberg, 1979, *Biochem. Biophys. Res. Comm.* 90(1): 347-354.

6.3 Example 3

The Exemplary Substance P Analog HOMSPERA® Stimulates Cellular Proliferation and Differentiation Following Radiation Treatment This study was done to determine the effect of treating irradiated mice with an exemplary substance P analog.

6.3.1. Materials and Methods

HOMSPERA® was provided by ImmuneRegen via CSBio, Inc. (Menlo Park, Calif., catalog number CS2663) as a lyophilized powder of the trifluoroacetate salt. The sample was stored at −20° C. until solubilized. HOMSPERA® was dissolved in dilute sterile saline and dilute acetic acid to obtain a solution of 300 μM concentration.

Seventy-two (72) Balb/c mice of age 5-6 weeks and normal physiological state (Taconic) were separated into 4 groups: Non-irradiated control (or Non-treatment control) (n=12), Irradiated control (vehicle controls) (n=20), Irradiated/Treated pre-exposure (n=20), and Irradiated/Treated post-exposure (n=20). Animals were housed individually in ventilated microisolator cages (4-5 mice per cage), fed ad libitum Lab Diet pellets, and acclimated for 5-7 days prior to treatment. On Day 1, animals were placed into the X-ray irradiator (RadSource 2000) for 4 minutes. Non-irradiated controls received no radiation exposure while the irradiated controls were exposed to radiation at the level of 1 Gy/minute. Animals were either treated with vehicle control or 300 μM HOMSPERA® in the same vehicle solution. The Non-irradiated control group and Irradiated control group were administered 25 μL of sterile saline intranasally daily for 7 days following radiation exposure. Animals treated with HOMSPERA® pre-radiation exposure were administered 25 μL of 300 μM solution intranasally 1 day prior to radiation exposure and daily thereafter for 7 days. Animals treated with HOMSPERA® post-radiation exposure were administered 25 μL of 300 μM solution intranasally daily for 7 days following radiation exposure as described in Table 2.

TABLE 2

Study Design

| Group | N | Vehicle Control | HOMSPERA ® Pre-treatment (Day 0) | HOMSPERA ® Post-treatment (Daily for 7 days) |
|---|---|---|---|---|
| 1. Non-irradiation control | 12 | X | | |
| 2. Irradiated control | 20 | X | | |
| 3. HOMSPERA ® | 20 | | X | X |
| 4. HOMSPERA ® | 20 | | | X |

Following radiation exposure, gross observations were made at least once daily. Animal body weights were recorded at Days 1, 2, 3, 4, 5, 9, and 12 for all irradiated animals. Three mice from each group, including controls, were sacrificed at each timepoint listed in Table 2 or when each mouse became moribund. The remaining mice, 8 each from the Irradiated control, Irradiated/Treated pre-exposure, and Irradiated/Treated post-exposure groups were observed for survival until Day 30 or when moribund.

TABLE 3

Blood collection timepoints

| Group | N* | Timepoints |
|---|---|---|
| Non-irradiated control (vehicle control) | 12 | q) 3-6 hours post irradiation of treatment group<br>r) 12-18 hours post $1^{st}$ collection<br>s) 24 hours post $2^{nd}$ collection<br>t) 48 hours post $3^{rd}$ collection |
| Irradiated control | 12 | u) 3-6 hours post irradiation<br>v) 12-18 hours post $1^{st}$ collection<br>w) 24 hours post $2^{nd}$ collection<br>x) 48 hours post $3^{rd}$ collection |
| HOMSPERA ® at Day 0 and daily for 7 days | 12 | y) 3-6 hours post irradiation<br>z) 12-18 hours post $1^{st}$ collection<br>aa) 24 hours post $2^{nd}$ collection<br>bb) 48 hours post $3^{rd}$ collection |
| HOMSPERA ® daily for 7 days | 12 | cc) 3-6 hours post irradiation<br>dd) 12-18 hours post $1^{st}$ collection<br>ee) 24 hours post $2^{nd}$ collection<br>ff) 48 hours post $3^{rd}$ collection |

*Three mice sacrificed per timepoint

Deaths and unanticipated adverse reactions were reported to the institutional veterinarian as soon as noted. The mice were sacrificed by regulated $CO_2$ upon the animal being moribund. Mice were considered moribund if one or more of the following criteria were met: 1) loss of body weight of 20% or greater in a 1 week period; 2) prolonged, excessive diarrhea leading to excessive weight loss (>20%); 3) persistent wheezing and respiratory distress; 4) extreme lethargy; 5) dehydration indicated by loose skin; 6) fever indicated by shivering or 7) prolonged or excessive pain or distress observed as prostration, hunched posture, paralysis, paresis, distended abdomen, ulcerations, abscesses, seizures or hemorrhages.

The percentage of animal mortality and time to death were recorded for every group in the study.

6.3.2. Results 6.3.2.1 Animal Body Weights

Animal body weights for non-irradiated controls were not recorded. Animal weights for all irradiated groups trended to decrease similarly to roughly 90% total body weight by Day 5 following radiation exposure. Animals exposed to radiation and treated with HOMSPERA® (post-irradiation treatment) were observed to have a slight recovery in lost body weight by Day 9. However, pre-irradiation treatment animals and irradiated control (vehicle control) animals continued to lose weight until moribund or sacrificed at Day 12. Irradiated control animals lost 16.1% (+/−1.6%) body weight at Day 12. Pre-irradiation treatment animals lost 20.2% (+/−2.4%) body weight at Day 12, while post-irradiation treatment animals lost 10.6% (+/−1.9%) body weight at Day 12.

6.3.2.2 CBC (Blood Differentials):

Blood differentials evaluated white blood cell (WBC), lymphocyte (LYM), monocytes (MON), granulocyte (GRA), red blood cell (RBC), and platelet (PLT) levels. Results are reported as cells/liter and normalized to the non-irradiated control group values.

6.3.2.3 Six Hours

White blood cell and lymphocyte levels trended to decrease significantly in irradiated animals. Animals pretreated with HOMSPERA® were observed to have lower lymphocyte counts than test non-irradiated control (vehicle control) and irradiated control animals. Monocyte and granulocyte counts in irradiated animals were observed to increase significantly for both the irradiated control group and the HOMSPERA® pre-treatment group. Monocytes increased about 200% over non-irradiated controls and granulocytes increased about 300% over non-irradiated controls. Red blood cell and platelet levels in irradiated animals were not found to differ significantly from non-irradiated controls.

6.3.2.4 24 Hours Post Exposure

White blood cell counts in irradiated animals continued to be lower than non-irradiated controls at 24 hours post-exposure. Animals treated with HOMSPERA® (both pre- and post-irradiation treatment) had white blood cell counts higher than that of the irradiated controls. Animals treated with HOMSPERA® post-radiation exposure were observed to have greater white blood cell counts than animals treated with HOMSPERA® prior to radiation exposure (about 30% versus about 19%). This same trend was observed in both lymphocyte (about 17% versus about 4%) and monocyte counts (about 119% versus about 95%). However, monocyte counts in HOMSPERA® treated animals were similar to those seen in non-irradiated control animals while irradiated control animals were observed to have a nearly 5 fold decrease in monocyte levels (about 100% versus about 20%). Granulocyte counts in animals treated with HOMSPERA® post exposure were significantly greater (about 158%) than those observed in non-irradiated controls (100%) and animals exposed to HOMSPERA® prior to radiation exposure (about 95%), while animals exposed to radiation and administered vehicle control were observed to have decrease granulocyte counts (about 75%). Again, red blood cell and platelet counts in irradiated animals were not observed to be significantly different from that seen in non-irradiated controls.

6.3.2.5 48 Hours Post Exposure

White blood cell counts in irradiated animals at 48 hours post-radiation exposure were very similar to those observed at 24 hours post-exposure. Again, irradiated controls were observed to have WBC counts lower than non-irradiated controls (about 17% versus 100%), while the post-radiation subjects had about double that amount (about 38%). Lymphocyte counts at 48 hours post-exposure mirrored those observed at 24 hours post-exposure. Animals treated post-radiation exposure had the highest lymphocyte levels (about 18%) of the three irradiated groups. Monocyte and granulocyte levels followed this trend as well. Animals treated with HOMSPERA® post-radiation exposure were observed to have monocyte and granulocyte levels greater than that of non-irradiated animals, control irradiated animals and pre-radiation treatment animals (about 120% vs. 100%, 38% and 75% for monocytes; 170% vs 100%, 78% and 102% for granulocytes). Red blood cell counts were not significantly different for animals exposed to radiation. However, animals exposed to radiation were observed to have significantly reduced platelet counts. Animals exposed to HOMSPERA®, either pre- or post-radiation exposure were observed to have platelet counts lower than that of control irradiated animals (about 40%).

6.3.2.6 96 Hours Post Exposure

White blood cell counts continued to decrease at 96 hours post-exposure. At this time point, irradiated animals treated with vehicle or HOMSPERA® pre-radiation exposure had white blood cell counts roughly $\frac{1}{25}^{th}$ that of non-irradiated controls (about 4%). Animals treated with HOMSPERA® following radiation exposure had white blood cell counts roughly 3 times greater (about 12%) than those observed in irradiated control animals. Interestingly, similar results were observed for lymphocytes, monocytes, and granulocytes. Monocyte and granulocyte levels in irradiated animals fell dramatically at 96 hours post-exposure compared to 48 hour results. Again, animals treated with HOMSPERA® following radiation exposure were observed to have substantially greater cell counts than those which were irradiated and treated with a vehicle control. Red blood cell counts continued to remain essentially unchanged. Platelet counts were observed to be similar to that seen at 48 hours post-radiation exposure. Nearly 50% reduction in platelet counts was observed in irradiated animals, and a small decreasing trend in HOMSPERA® treated animals.

6.3.2.7 Flow Cytometry

Flow cytometry was conducted to identify and quantify cell markers in the animal groups but the results did not reveal conclusive trends. For example, non-irradiated control animals were observed to have a significant variance in positive CD34 cells and positive Sca-1 cells over the 4 time points measured (6, 18, 24, and 48 hours). Non-irradiated controls were observed to have a decreasing trend in percent positive CD 117 and CD9 cells. Similar results were observed in irradiated animals.

6.3.3. Discussion

A study was executed to evaluate the physiological effects of radiation and treatment with HOMSPERA® (intranasally administered 254 of 300 µM solution) on mice. Mice were grouped into non-irradiated controls, irradiated controls, irradiated/treated pre-exposure, and irradiated/treated post-exposure. Irradiated animals were exposed to 4 Gy X-ray irradiation at a rate of 1/Gy per minute. Irradiated animals not treated with HOMSPERA® were observed to have dramatic losses in body weight and significant decreases in CBC markers.

Animals treated with HOMSPERA® for 8 days, beginning 1 day pre-radiation exposure, were observed to have weight losses greater than that of irradiated/non-treated animals. Alternatively, animals treated with HOMSPERA® for 7 days following radiation exposure were observed to have a decreased weight reduction in comparison to irradiated controls.

Animals exposed to radiation were observed to have a significant reduction in white blood cell counts, lymphocyte counts, monocyte counts, granulocyte counts, and platelet counts. Most of these effects were observed as early as 6 hours post-radiation exposure; however decreases in platelet levels were not observed until 48 hours post-exposure. Treatment with HOMSPERA® prior to radiation exposure (and 7 days thereafter) resulted in increases in white blood cell, lymphocyte, monocyte, and granulocyte counts when compared to irradiated controls. However, treatment with HOMSPERA® for 7 days beginning after exposure to radiation was observed to have even greater effects on these same cell types. Animals treated with HOMSPERA® following radiation exposure were observed to have greater monocyte and granulocyte counts than non-irradiated control animals for the first 48 hours following radiation exposure. However, these effects were not seen at 96 hours post-exposure, as monocyte and granulocyte counts were dramatically reduced.

Analysis of flow cytometry data did not reveal conclusive trends for any of the groups tested. Non-irradiated control animals were observed to have a level of variance similar to that seen in irradiated/drug-treated animals. This may be a product of biological variance, equipment variance, or both.

Animals exposed to radiation were observed to have a dramatic decrease in weight that continued until sacrifice or death. Animals treated with HOMSPERA® daily for 7 days following irradiation were observed to have significantly less weight loss. The post-irradiation treatment group was also observed to have significantly increased levels of white blood cells, lymphocytes, monocytes and granulocytes when compared to irradiated control animals and pre-irradiation treatment animals. Platelet levels were observed to decrease significantly in all irradiated animals after 48 hours post-exposure. Treatment with HOMSPERA® for 7 days following radiation exposure yielded the most efficacious method of maintaining animal weights and increasing vital CBC markers.

6.4 Example 4

The Effect of an Exemplary Substance P Analog, Homspera®, on Cellular Differentiation and Proliferation

6.4.1. Introduction

In the study described below, human bone marrow-derived hematopoietic cell populations (or hematopoietic stem cells, HSCs) were cultured with or without HOMSPERA® to determine whether HOMSPERA® affects proliferation or differentiation of the cells.

To assess proliferation, intracellular ATP (iATP) levels were measured. Increased levels of iATP correlate with increased cellular proliferation, because cells that are proliferating typically require high levels of energy, which is provided by iATP.

To examine or assess proliferation, in this case, the experiment was designed to compare the effects of HOMSPERA® on proliferation and differentiation after a 14 day incubation period. Although more or increased concentrations of cytokines or growth factors are typically added to support differentiation than proliferation alone-these concentrations are still effective for proliferation. Therefore proliferation was examined under the same conditions as those used for differentiation.

To induce differentiation "optimal" concentrations of growth factors and cytokines were used. Rich, 2003, *Curr. Op. Drug Discovery Devel.* 6:100-109, Rich and Hall, 2005, *J. Tox. Sci.* 87(2): 427-441. However, because substance P is known to stimulate hematopoiesis and promote the release of cytokines that contribute to differentiation, "suboptimal" concentrations of growth factors and cytokines were also used in the even the effects of HOMSPERA® wouldn't be observed under saturating and therefore optimal cytokine conditions. Suboptimal concentrations were approximately one-fifth of optimal concentrations and were concentrations known to support colony formation. Rich, personal communications.

6.4.2. Methods

HOMSPERA® (5 mg, Lot E844) was shipped as a solid compound. The compound was dissolved in 1 ml of Iscove's Modified Dulbecco's Medium (IMDM) and a serial dose response prepared in single log doses so that the final dose in culture ranged from 1 nM to $1 \times 10^{-16}$ M. All working dilutions were performed in IMDM.

Starting with human bone marrow aspirate, the mononuclear cell (MNC) fraction was separated from the whole bone marrow using Ficoll-Paque density gradient centrifugation. The resulting MNC fraction had a cell concentration of $6.2 \times 10^6$ cells/ml with a viability of 99.9%. The cell concentration was adjusted so that the final cell concentration in culture was 10,000 cells/well.

Human bone marrow MNC was dissolved in IMDM and cultured at a concentration of 10,000 cell/well in a CAMEO™-96 Master Mix (HemoGenix, Inc., Colorado Springs, Colo.). Master Mix is a HemoGenix proprietary cell culture media comprised of a serum mix (4 parts), a methyl cellulose mix (4 parts) and a growth factor mix (1 part) with the bone marrow target cells (1 part). See, Rich and Hall 2005, *Toxicol. Sci.* 87(2): 427-441.

Different combinations and concentrations of growth factors are used to induce differentiation of cells into specific cell types. The target cell populations were: High Proliferative Potential-Stem and Progenitor cell (HPP-SP), Colony-forming Cells-Granulocyte, Erythroid, Macrophage, Megakaryocyte (CFC-GEMM), Blast Forming Unit-Erythroid (BFU-E), Granulocyte-Macrophage-Colony Forming Cells (GM-CFC), Megakaryocyte-Colony Forming Cells (Mk-CFC), T-lymphocyte-Colony Forming Cells (T-CFC), B-lymphocyte-Colony Forming Cells (B-CFC).

Growth factors or cytokines used in the study were: erythropoietin (EPO), granulocyte macrophage-colony stimulating factor (GM-CSF), granulocyte-colony stimulating factor (G-CSF), Interleukins 3, 6, 2 and 7 (IL-3, IL-6, IL-2 and IL-7), stem cell factor (SCF), thrombopoietin (TPO) and soluble mutant flt3 ligand (Flt3-L).

The concentrations of growth factors or cytokines used for each cell type assay are provided in Table 4 (Optimal Growth Concentrations) and Table 5 (Sub-Optimal Growth Concentrations).

TABLE 4

Optimal Growth Factor or Cytokine Concentrations for 7 Cell Populations (/ml)

|  | EPO | GM-CSF | G-CSF | IL-3 | IL-6 | SCF | TPO | Flt3-L | IL-2 | IL-7 |
|---|---|---|---|---|---|---|---|---|---|---|
| HPP-SP | 3 U | 20 ng | 20 ng | 10 ng | 20 ng | 50 ng | 50 ng | 50 ng | 50 ng | 40 ng |
| CFC-GEMM | 3 U | 20 ng | 20 ng | 10 ng | 20 ng | 50 ng | 50 ng | 50 ng | — | — |

TABLE 4-continued

Optimal Growth Factor or Cytokine Concentrations for 7 Cell Populations (/ml)

|        | EPO | GM-CSF | G-CSF | IL-3  | IL-6 | SCF   | TPO   | Flt3-L | IL-2  | IL-7  |
|--------|-----|--------|-------|-------|------|-------|-------|--------|-------|-------|
| BFU-E  | 3 U | —      | —     | 10 ng | —    | 50 ng | —     | —      | —     | —     |
| GM-CFC | —   | 20 ng  | —     | 10 ng | —    | 50 ng | —     | —      | —     | —     |
| Mk-CFC | —   | —      | —     | 10 ng | —    | 50 ng | 50 ng | —      | —     | —     |
| T-CFC  | —   | —      | —     | —     | —    | —     | —     | —      | 50 ng | —     |
| B-CFC  | —   | —      | —     | —     | —    | —     | —     | —      | —     | 40 ng |

TABLE 5

Sub-Optimal Growth Factor or Cytokine Concentrations for 7 Cell Populations (/ml)

|          | EPO    | GM-CSF | G-CSF  | IL-3   | IL-6   | SCF  | TPO  | Flt3-L | IL-2 | IL-7   |
|----------|--------|--------|--------|--------|--------|------|------|--------|------|--------|
| HPP-SP   | 0.06 U | 0.4 ng | 0.4 ng | 0.2 ng | 0.4 ng | 1 ng | 1 ng | 1 ng   | 1 ng | 0.8 ng |
| CFC-GEMM | 0.06 U | 0.4 ng | 0.4 ng | 0.2 ng | 0.4 ng | 1 ng | 1 ng | 1 ng   | —    | —      |
| BFU-E    | 0.06 U | —      | —      | 0.2 ng | —      | 1 ng | —    | —      | —    | —      |
| GM-CFC   | —      | 0.4 ng | —      | 0.2 ng | —      | 1 ng | —    | —      | —    | —      |
| Mk-CFC   | —      | —      | —      | 0.2 ng | —      | 1 ng | 1 ng | —      | —    | —      |
| T-CFC    | —      | —      | —      | —      | —      | —    | —    | —      | 1 ng | —      |
| B-CFC    | —      | —      | —      | —      | —      | —    | —    | —      | —    | 0.8 ng |

U = Unit,
ng = nanogram

The sub-optimal concentrations were about 50 fold less than the optimal concentrations used.

Eleven μl of the diluted HOMSPERA® solution was added to each well followed by 100 μl of the master mix for each cell population detected. The cells were incubated in the absence or presence of HOMSPERA® under sub-optimal and optimal stimulatory conditions for 7 target cell populations in 96-well plates for 14 days at 37° C. in a fully humidified atmosphere comprised of 5% $CO_2$ and 5% $O_2$. The total colony counts were manually enumerated under an inverted microscope, followed directly by processing the plates for bioluminescence to determine the intracellular ATP concentrations of the cells in each well. The study was concluded within 30 days of obtaining HOMSPERA® and within 14 days of obtaining the human bone marrow aspirate.

Prior to processing all 96-well plates, the total colony counts/well were manually enumerated by microscopy. The mean, standard deviation and percent coefficient of variation was calculated for all groups, transposed and plotted. The intracellular ATP (iATP) concentration was measured after manual enumeration. The output of the luminometer is non-standardized Relative Luminescence Units (RLU). Prior to measuring the samples, an ATP standard curve was performed. This allowed the RLU values to be automatically calculated into standardized ATP (μM) units. For both the RLU and ATP values derived from each well, the luminometer software calculated the mean, standard deviation and percent coefficient of variation.

6.4.3. Results

The data indicate HOMSPERA® stimulates proliferation or differentiation of hematopoietic stem cells (HSCs) isolated from human bone marrow MNCs. HOMSPERA® stimulated proliferation as indicated by the increase in iATP. HOMSPERA® also stimulated differentiation as indicated by the increased colony forming units of hematopoietic progenitor cells.

Some background is helpful to understanding the results. A traditional CFC assay is usually performed in duplicate in 35 mm Petri dishes. Sub-optimal growth factor studies cannot be performed with commercial media. Instead, the individual reagents have to be prepared and added individually. In this study, optimum growth factor/cytokine concentrations would be those that are normally used for the CFC assay. This assay is a functional differentiation assay, meaning that the assay relies on the functional ability of the target cells to divide and differentiate into colonies containing cells that identify the types of colonies being produced. Many lineage-specific growth factors, e.g. EPO, GM-CSF, TPO, are known to exhibit bifunctionality in that they will act as a proliferation factor for primitive cells in the series, but as a survival factor for the differentiating and maturating cells. Without the factors, the cells will enter into apoptosis. To induce proliferation, lower concentrations of growth factors or cytokines are required. These concentrations will, in many cases, be sub-optimal for the CFC differentiation assay. If proliferation only had been measured using the ATP assay at 7 days rather than 14 days, it is possible that a different response might have been observed using optimal and sub-optimal growth factor/cytokine concentrations. For the 7 cell populations detected in this study, the growth curve at 14 days indicates that proliferation decreased as differentiation increased. Therefore, the iATP concentration detected at 14 days represents residual proliferation within the colonies. However, since both the CFC and ATP assays were performed under the same conditions, it is possible to directly compare the results from the two separate readouts. Taking these factors into account, the response between the 7 cell populations is probably best described as a percentage of the respective control.

6.4.3.1 Controls

The control values after 14 days in culture are shown in Table 6 and Table 7. In most cases, the control results are within the expected range of values with the cell populations falling into three categories: stem cell populations, myelopoietic populations and lymphopoietic populations. The 2 stem cell populations (HPP-SP and BFU-E) show the greatest proliferation and differentiation potential followed by the 3 myelopoietic populations (CFC-GEMM, GM-CFC and Mk-CFC) and the 2 lymphopoietic populations (T-CFC and B-CFC).

TABLE 6 iATP Proliferation Assay Controls

| | Optimal Conditions | | Sub-Optimal Conditions | |
|---|---|---|---|---|
| | Mean | Std. Dev. | Mean | Std. Dev. |
| Background | 0.213 | 0.021 | 0.320 | 0.026 |
| HPP-SP | 0.591 | 0.088 | 0.802 | 0.254 |
| CFC-GEMM | 0.31 | 0.078 | 0.815 | 0.157 |
| BFU-E | 0.664 | 0.077 | 0.781 | 0.199 |
| GM-CFC | 0.525 | 0.144 | 0.914 | 0.03 |
| Mk-CFC | 0.483 | 0.057 | 0.655 | 0.22 |
| T-CFC | 1.165 | 0.208 | 0.649 | 0.158 |
| B-CFC | 0.691 | 0.105 | 0.417 | 0.109 |

TABLE 7

CFC Differentiation Assay Controls

| | Optimal Conditions | | Sub-Optimal Conditions | |
|---|---|---|---|---|
| | Mean | Std. Dev. | Mean | Std. Dev. |
| Background | 6.8 | 1.0 | 16.8 | 3.9 |
| HPP-SP | 109.0 | 7.8 | 74.7 | 12.4 |
| CFC-GEMM | 94.0 | 7.4 | 56.8 | 5.0 |
| BFU-E | 114.8 | 168.1 | 24.5 | 10.4 |
| GM-CFC | 53.7 | 4.1 | 50.7 | 9.5 |
| Mk-CFC | 38.7 | 12.2 | 38.2 | 7.2 |
| T-CFC | 38.5 | 6.3 | 15.0 | 1.8 |
| B-CFC | 22.8 | 2.1 | 17.5 | 3.0 |

6.4.3.2 Effect of HOMSPERA® on Differentiation

In the presence of optimal growth factors, all cell populations, with the exception of BFU-E, exhibited enhancement or potentiation in differentiation potential. The response of BFU-E was significantly lower than the controls at all compound doses, although a slight increase from the lowest dose at $10^{-16}$M to $10^{-13}$M was observed prior to a decrease to the highest dose used (1 nanoMolar (nM)). For B-CFC, the dose response was a bell-shaped curve, beginning below control values at $10^{-16}$M, but peaking at 1 picomolar (pM) at about 163%, prior to decrease to control values. The Mk-CFC and CFC-GEMM populations also increased from control values at the lowest dose to reach peak between $10^{-14}$M and $10^{-13}$M respectively before decrease to control values at the highest dose of HOMSPERA®. HPP—SP, T-CFC and GM-CFC all started at values significantly higher than control at the lowest dose. The T-CFC produced an approx. plateau between $10^{-16}$M and $10^{-13}$M before decreasing to control levels. The HPP-SP population peaked at $10^{-15}$M and decreased thereafter to control values. The GM-CFC produced the greatest potentiation of all cell populations peaking at $10^{-14}$M.

Under sub-optimal growth factor/cytokine conditions, both GM-CFC and CFC-GEMM produced a dose response that peaked at $10^{-14}$M and decreased thereafter, although at the highest dose of 1 nM, the values from these two population did not fall below control values. In contrast, the B-CFC and HPP-SP populations, produced a very gradual increase with a slight decrease at 1 nM. The T-CFC hovered around control values and exhibited a decrease to below control values after $10^{-13}$M. Both the BFU-E and Mk-CFC were below control values for essentially the whole dose response, although a peak did occur at $10^{-14}$M for Mk-CFC and $10^{13}$M for BFU-E. For those populations that exhibited values greater than control at the lowest dose used, the dose response could be extended to doses lower than $10^{-16}$M.

6.4.3.3 Effect of HOMSPERA® on Proliferation

The ATP proliferation assay shows a different profile to that of the differentiation assay for all cell populations. Like the CFC assay at optimum growth factor/cytokine conditions, BFU-E exhibited a dose response below control values, with a gradual increase to control values at the highest dose used. The dose response for T-CFC was essentially flat at control levels. The B-CFC exhibited a flat dose response over the complete dose range, but at approx. 200% of control values. All other populations, (HPP-SP, CFC-GEMM, GM-CFC and Mk-CFC) exhibited an unusual U-shaped dose response curve, decreasing from the lowest HOMSPERA® dose to about $10^{-14}$M and increasing again from about 10 fM to 1 nM.

At sub-optimal growth factor/cytokine concentrations, only the lymphopoietic cell populations (T-CFC and B-CFC) exhibited a potentiation between 200 and 300% above control values. However, for both of these cell populations, the dose response was essentially flat. The Mk-CFC population exhibited essentially no response, while HPP-SP, CFC-GEMM, BFU-E and GM-CFC exhibited dose responses that were below control levels for most of the doses used.

However, although B-CFC are enhanced under optimal and sub-optimal condition in the ATP proliferation and T-CFC are enhanced under sub-optimal conditions also in the ATP proliferation assay, this enhancement effect is not dose-dependent, at least over the dose range used. The absence of a dose response indicates that the response observed may actually be a plateau effect and that the cell populations are sensitive to the compound at much lower doses than were tested in this study. In addition, these cells do not demonstrate toxicity at the levels tested.

6.4.4. Discussion

After 14 days of incubation, HOMSPERA® exhibited its maximum effect on the differentiation, rather than the proliferation process. Notable, for most of populations, was the apparent absence of distinct cytotoxicity. For both the CFC differentiation and ATP proliferation assays, the BFU-E population was the only population that was suppressed under optimal and sub-optimal conditions. However, see Example 5, below, where BFU-E differentiation and/or proliferation was enhanced.

The GM-CFC exhibited the greatest enhancement in the CFC differentiation assay, a result which is in accordance with published data for substance P. The T-CFC and B-CFC exhibit a dose response in the CFC differentiation assay under optimal and sub-optimal conditions. However, although B-CFC are enhanced under optimal and sub-optimal condition in the ATP proliferation and T-CFC are enhanced under sub-optimal conditions also in the ATP proliferation assay, this enhancement effect is not dose-dependent, at least over the dose range used. The absence of a dose response indicates that the response observed may actually be a plateau effect and that the cell populations are sensitive to the compound at much lower doses than were tested in this study. In addition, these cells do not demonstrate toxicity at the levels tested.

Several of the effects observed using the CFC differentiation readout have also been found for substance P and published in the literature. The difference between results of the ATP proliferation assay and the CFC differentiation assay is noteworthy. Firstly, higher doses of HOMSPERA® enhance differentiation rather than proliferation, an effect known for lineage-specific growth factors, for example, erythropoietin. Secondly, for most lympho-hematopoietic cell populations exposed to the present dose range, the primary effect of HOMSPERA® is during differentiation or maturation.

For those populations that exhibited values greater than control at the lowest dose used, the dose response could be extended to doses lower than $10^{-16}$M. In evaluating the colony numbers prior to detecting iATP, it did appear that the change in colony numbers was due to a change in the size of the colonies as the compound dose increased. This was particularly the case for the HPP-SP population.

HOMSPERA® was effective at stimulating differentiation of several hematopoietic progenitor cells under both optimal and sub-optimal growth factor conditions. Under sub-optimal conditions HPP-SP, GM-CFC, CFC-GEMM and B-CFC were noticeably stimulated to differentiate. Under optimal conditions, HPP-SP, GM-CFC, T-CFC, Mk-CFC, CFC-GEMM and B-CFC progenitor cells were stimulated to differentiate.

Granulocyte/macrophage progenitors were the most responsive to HOMSPERA® and were stimulated approximately 250% and 200% above controls lacking HOMSPERA® treatment for both optimal and sub-optimal growth factor conditions respectively. CFC-GEMM cells were also stimulated to surprising levels above controls at about 175% in optimal conditions and about 225% in sub-optimal conditions. HPP-SP and T-CFC cell numbers were both about 175% above control values for optimal conditions. Under sub-optimal conditions, T-CFC populations did not change much from control values, whereas HPP-SP populations were enhanced roughly 125% from the population controls. In optimal conditions, B-CFC was 160% above control populations at HOMSPERA® concentration of about $10^{-12}$M. The effects of HOMSPERA® on B-CFC cells was not as pronounced under sub-optimal conditions, and were only stimulated 125% from the control population.

HOMSPERA® was also effective at stimulating proliferation as measured by iATP levels using a fluorescent read-out. The most notable effects of HOMSPERA® were on B-CFC and T-CFC progenitors cultured under sub-optimal cytokine levels. B-CFC iATP levels increased nearly 300% from control populations lacking HOMSPERA® and T-CFC iATP levels increased 200% from controls. Furthermore HOMSPERA® is effective at the lowest dose tested, $10^{-16}$M, suggesting biological activity for proliferation at sub-femtomolar concentrations. The results for the optimal growth factor conditions are similar to the differentiation assays in that the same cell types were stimulated with HOMSPERA® (HPP—SP, GM-CFC, T-CFC, Mk-CFC, CFC-GEMM and B-CFC progenitor cells). B-CFC iATP levels were again significantly higher than controls (200%).

6.5 Example 5

The Effect of an Exemplary Substance P Analog, HOMSPERA®, on Cellular Differentiation and Proliferation (Multi-Donor Study)

The study was undertaken to further illustrate lympho-hematopoietic differentiation in response to HOMSPERA® using human-derived hematopoietic cell populations from three different bone marrow donors.

HOMSPERA® (5 mg, Lot F209) was shipped as a solid compound and stored at 4° C. upon arrival. Compound was dissolved in 1 ml of Iscove's Modified Dulbecco's Medium (IMDM) and a serial dose response was prepared in single log doses so that the final dose in culture ranged from 1 nanoMolar (nM) to $1\times10^{-16}$ M. All working dilutions were performed in IMDM. Cell cultures from each donor were started at different times and a fresh solution of HOMSPERA® was prepared for each individual experiment.

Starting with human bone marrow aspirate, the mononuclear cell (MNC) fraction from each aspirate was separated from whole bone marrow using Ficoll-Paque density gradient centrifugation.

The colony-forming cell (CFC) assay was performed using optimal growth factor/cytokine concentrations. The reagents and conditions were similar to those used in Example 4, except that no ATP measurements were performed. The MNC fraction from each bone marrow donor was dissolved in IMDM and cultured at a concentration of 5,000 cells/well in a Culture Master Mix (HemoGenix, Inc., Colorado Springs, Colo.).

The target cell populations were: High Proliferative Potential-Stem and Progenitor cell (HPP-SP), Colony-Forming Cells-Granulocyte, Erythroid, Macrophage, Megakaryocyte (CFC-GEMM), Blast Forming Unit-Erythroid (BFU-E), Granulocyte-Macrophage-Colony Forming Cells (GM-CFC), Megakaryocyte-Colony Forming Cells (Mk-CFC), T-lymphocyte-Colony Forming Cells (T-CFC), B-lymphocyte-Colony Forming Cells (B-CFC).

Growth factors or cytokines used in the study were: erythropoietin (EPO), granulocyte macrophage-colony stimulating factor (GM-CSF), granulocyte-colony stimulating factor (G-CSF), Interleukins 3, 6, 2 and 7 (IL-3, IL-6, IL-2 and IL-7), stem cell factor (SCF), thrombopoietin (TPO) and soluble mutant Flat 3 ligand (Flt3-L).

The concentrations of growth factors or cytokines used for the CFC assay are the same as those provided in Table 4 of Example 4, e.g., Optimal conditions.

The assay was performed in a 96-well plate. To each well, 11 μl of the test compound (HOMSPERA®) dilution was added followed by 100 μl of the Culture Master Mix for each cell population detected. Cultures were incubated for 14 days at 37° C. in a fully humidified atmosphere containing 5% $CO_2$ and 5% $O_2$. Thereafter, the total colony counts were manually enumerated under an inverted microscope.

The mean, standard deviation and percent coefficient of variation was calculated for all groups, transposed and plotted as a function of donor. The percent from control values were calculated and also plotted as a function of donor. In addition, results were compared from each individual cell population from all donors. All results were plotted using Prism Version 5 for Mac.

6.5.1. Results: Response from Individual Cell Populations 6.5.1.1 Stem Cells:

For all three donors, the primitive HPP-SP stem cells exhibited a greater response than the more mature multi-potential CFC-GEMM stem cells. Variations with respect to the level of potentiation did occur; and at the highest doses, a decrease in colony counts was usually observed. For example, with the HPP-SP cells, donor 1 was stimulated to approx. 300% from controls at HOMSPERA® concentrations of $10^{-12}$ M and $10^{-11}$ M, while donors 2 and 3 were approx. 200% and 175% from controls respectively. Both donors 2 and 3 were maximally stimulated at $10^{-15}$ M HOMSPERA®, a concentration lower than that for donor 1.

The variation between donors for CFC-GEMM was less pronounced and the trend was similar to levels previously observed with optimal growth factors in Example 4. Donor 1 exhibited the greatest potentiation to greater than 200% from controls, while donors 2 and 3 were both around 175% from controls. For all three donors, the maximum effects of HOMSPERA® were observed at the $10^{-14}$ M dose.

6.5.1.2 Hematopoietic Lineage Cells:

For the GM-CFC population, donors 1 and 2 demonstrated responses above background, while donor 3 was very close to control levels for nearly all the HOMSPERA® concentrations tested. Both donors 1 and 2 were maximally stimulated to 200% and 150% relative to controls at $10^{-13}$ M HOMSPERA®, respectively. The trend observed for GM-CFC is similar to that from the single marrow donor study. Additionally, the two-fold enhancement of colony forming activity and effectiveness at low HOMSPERA® concentrations is consistent with the multi-donor study of Example 6.

This study showed that for all three donors, BFU-E exhibited a response that was in most cases significantly greater than the control over the entire HOMSPERA® dose range. Indeed BFU-E showed the greatest response of all cell populations from the second donor at $10^{-11}$ M HOMSPERA®. Colony numbers were enhanced to approx. 150-300% relative to controls, depending on the donor. These levels of stimulation are consistent with the multi-donor study of Example 6, examining the effects of HOMSPERA® on BFU-E colony formation.

The Mk-CFC population also exhibited a varied dose response to HOMSPERA®. However, whereas donor 1 demonstrated an overall increase in potentiation with increasing compound dose, the response of donors 2 and 3 was relatively flat, and that from donor 3 was either below or near control levels over the HOMSPERA® doses examined. While the concentration for maximal stimulation varies between donors, donors 1 and 2 both stimulated megakaryocyte colony formation greater than 200% from controls.

6.5.1.3 Lymphopoietic Cell Populations:

These two populations demonstrated the greatest effects of HOMSPERA® with donor 1. The T-CFC response was greater than 300% from controls and greater than 200% for B-CFC for donor 1. However, the maximum effect of HOMSPERA® on donors 2 and 3 was less than 150% from controls. T-CFC for donors 2 and 3 demonstrated a gradual increase with increasing compound dose, but the B-CFC demonstrated a slight decrease with increasing compound dose. The T-CFC population for Donors 2 and 3 exhibited a maximum at 0.1 picoMolar ($10^{-12}$M), slightly above control values. For Donors 2 and 3, the peak value occurred at $1\times10^{-15}$M.

6.5.2. Conclusions

The overall response of the three donors was that HOMSPERA® potentiates differentiation of all seven cell populations tested when stimulated with optimal growth factor and cytokine concentrations. There was no apparent toxicity at the highest doses.

HOMSPERA® is effective at increasing colony formation of the multi-lineage progenitor CFC-GEMM, and consistently acts to stimulate the colonies produced from CFC-GEMM.

6.6 Example 6

An Exemplary Substance P Analog, HOMSPERA®, Stimulates Proliferation of Exemplary Adult Stem Cells, Human Bone Marrow Cells (HBMCs)

The objective of this study was to compare stem cell hematopoiesis of HOMSPERA® with native, C-terminally amidated substance P using human bone marrow cells in vitro.

6.6.1. Materials and Methods

Colony forming unit (CFU) assays were used to examine the effects of HOMSPERA® in stimulating hematopoietic stem cells isolated from human bone marrow to differentiate into lineage-specific progenitor cells. As stem cells differentiate in response to growth factors, they form a colony of cells with distinct morphologies that can be visualized using a microscope. This study examined the formation of three different progenitor cell populations, erythrocytes, platelets and granulocytes/macrophages.

Bone marrow aspirates were obtained from three healthy donors between 18 and 35 years of age following appropriate guidelines and protocols. Bone marrow mononuclear cells were isolated using a Ficoll-Hypaque density gradient, separating red blood cells from the others. Cells from each donor were processed independently and used for setting up individual experiments to assess the effects, if any, of donor variability.

Cells ($1\times10^5$) were plated in duplicate onto 35 mm tissue culture plates for each condition tested and set up as described in Rameshwar et al. 1993, *Blood*. 81:2, 391-398. Erythroid and granulocyte/macrophage cultures were plated using methylcellulose and megakaryocyte cultures (platelet precursors) used a collagen-based support (StemCell Technologies, Vancouver, Canada, catalogue #04973). Cells were cultured in the presence of either HOMSPERA® or substance P at various concentrations. In the platelet study, neurokinin receptor antagonists were used to demonstrate receptor-specific effects. CP 99,994 (Pfizer) was used as a neurokinin-1 receptor antagonist and SR 48968 (Sanofi) was used as a neurokinin-2 receptor antagonist.

The cytokines and growth factors added to Blast Forming Unit—Erythroid (BFU-E) cultures, Colony Forming Unit—Erythroid (CFU-E) cultures, and Colony Forming Unit—Granulocyte/Macrophage (CFU-GM) cultures were added as defined by proliferative units. BFU-E cultures contained 2 Units human interleukin-3 (hIL-3) and 2 Units recombinant human erythropoietin (rhEpo). Two Units IL-3 is about 0.1 ng/3 ml. Rameshwar, private correspondence. CFU-E cultures contained 2 Units rhEpo, and CFU-GM cultures contained 2.6 Units recombinant human granulocyte macrophage-colony stimulating factor (GM-CSF). The Units of GM-CSF (2.6) is about 2 ng/3 ml. Rameshwar, private correspondence.

The biological activity in proliferative units for Epo was characterized by R&D Systems, Inc. in a cell proliferation assay using TF-1 cells, a factor-dependent human erythroleukemic cell line. Kitamura, et al., 1989, *J. Cell. Physiol.* 140: 323-334. The units for hIL-3 and GM-CSF were defined using an IL-3/GM-CSF-dependent cell line, M-07e, a subline of the M-07 human megakaryoblastic leukemia cell line. Avanzi, G et al., 1990, *J. Cell. Physiol.*, 145:458-464. Standard growth curves were established using serial dilutions of rhIL-3 (50 ng/ml) or rhGM-CSF (1 ng/ml). One cytokine proliferative unit was defined as the amount required to stimulate one-half maximal growth of the M-07e cells.

Cultures were set up with limited cytokines and growth factors which would promote differentiation of one progenitor per plate. Growth factors and cytokines added to Colony Forming Unit—Megakaryocyte (CFU-Mk) cultures used weight/volume ratios and included 50 ng/ml recombinant human thrombopoietin (rhTpo), 10 ng/ml recombinant human interleukin-6 (rhIL-6), and 10 ng/ml recombinant human interleukin-3 (rhIL-3) as suggested and supplied by StemCell Technologies.

Cells were cultured in the presence of HOMSPERA® or substance P over the following molar concentrations: $10^{-7}$, $10^{-8}$, $10^{-9}$, $10^{-10}$, $10^{-11}$, $10^{-12}$, $10^{-13}$, and $10^{-14}$M. Each compound was dissolved in endotoxin-free water to a final concentration of 0.1 mM. After reconstitution, the solutions were aliquoted into siliconized microcentrifuge tubes and exposed to nitrogen gas, eliminating oxygen in the head space of the enclosure. All aliquots were stored at −20° C. until use and used within one month of reconstitution. See, Rameshwar, et al. 1997, *J. Immunol.* 158:3417-3424.

Control plates without HOMSPERA® or substance P were used to assess the baseline for colony growth. Cultures were incubated at 37° C. with 5% $CO_2$ for approximately 14 days, after which colonies were manually enumerated using a microscope. To count megakaryocyte colonies, the cells were fixed followed by a staining procedure using the following antibodies: primary—mouse anti-human GP11b/111a, isotype control—mouse anti-trinitrophenyl, secondary—biotin-conjugated goat anti-mouse IgG, detection—avidin-alkaline phosphatase conjugate.

The results are expressed as percent colonies of control cultures (without HOMSPERA® or substance P). The number of control colonies were normalized to 100% and represented as a zero level on the Y-axis.

6.6.2. Results

HOMSPERA® was more effective than substance P at increasing colony counts for all stem cell progenitors examined. Two different red blood cell progenitor types were examined, BFU-E and CFU-E, which derive from a common progenitor, colony forming unit-granulocyte erythrocyte macrophage megakaryocyte (CFU-GEMM). BFU-E mature into CFU-E, which ultimately develop into functional red blood cells. (FIGS. 1 & 2)

HOMSPERA® was more effective than substance P at enhancing stem cell differentiation. HOMSPERA® enhanced BFU-E colony formation 2-fold (or 100%) relative to controls, whereas substance P increased colonies about 1.5-fold (or 60%) from control values (FIG. 1). These effects are similar to those of Example 5.

For CFU-E, the difference between HOMSPERA® and substance P treatment was less pronounced. For example, HOMSPERA® enhanced colony formation to greater than 80% from control values, while substance P enhanced colony formation to about 70% from control values (FIG. 2).

This study demonstrated greater than a 2-fold increase in granulocyte/macrophage precursors when cultured with several different HOMSPERA® concentrations from $10^{-13}$ to 10-9M (FIG. 3), and HOMSPERA® was twice as effective as substance P at stimulating differentiation of human stem cells into CFU-GM. These results suggest that HOMSPERA® could increase circulating levels of granulocytes and macrophages in vivo, possibly acting to mobilize the progenitors from the bone marrow or through a combination of differentiation and mobilization. The two-fold stimulation is similar to levels observed in Example 5.

HOMSPERA® and substance P treatments each demonstrated approximately a 2-fold stimulatory effect above controls for platelet precursors. However, HOMSPERA® was effective at a concentration one log unit below substance P ($10^{-9}$ M vs. $10^{-8}$ M). To demonstrate that the effects of substance P were occurring through activation of the neurokinin-1 receptor, two different receptor antagonists were used in the presence of substance P. CP-99,994 is a neurokinin-1 receptor antagonist which blocks the stimulatory activity of substance P. Additionally, a neurokinin-2 receptor antagonist SR48968 was used, which showed no effect on substance P activity in enhancing platelet colony formation indicating that the effects of substance P on Mk colonies are via the neurokinin-1 receptor. The effects of HOMSPERA® on platelet precursors is similar to the two-fold levels observed in Example 5.

6.6.3. Conclusion

These data indicate HOMSPERA® can stimulate hematopoiesis of all 3 major blood cell types. HOMSPERA® was effective at concentrations ranging from $10^{-7}$M to $10^{-14}$M. In addition, HOMSPERA® was more potent than substance P in enhancing colony formation of BFU-E, CFU-E, CFU-GM and CFU-Mk.

While the methods and compositions have been described with respect to specific examples including presently preferred modes of carrying out certain embodiments, those skilled in the art will appreciate that there are numerous variations and permutations of the above described systems and techniques that fall within the spirit and scope of the invention as set forth in the appended claims.

All references cited herein are incorporated herein by reference in their entireties for all purposes.

What is claimed is:

1. A method of treating myelodysplastic syndrome in a human comprising administering to a human in need thereof an effective amount of a substance P analog consisting of $Z_1$-RPKPQQFFMeGIyLM($O_2$)-$Z_2$, wherein $Z_1$ is $NH_2$ and $Z_2$ is C(O)$NH_2$ (SEQ ID NO: 11).

2. The method of claim 1 wherein the myelodysplastic syndrome is refractory anemia, refractory anemia with ringed sideroblasts, refractory cytopenia with multilineage dysplasia, refractory cytopenia with multilineage dysplasia and ringed sideroblasts, refractory anemia with excess blasts I and II, 5q syndrome or myelodysplasia unclassifiable.

3. The method of claim 2, wherein the myelodysplastic syndrome is refractory anemia with excess blasts I and II.

4. The method of claim 1 wherein administration of the substance P analog results in an increase in leukocytes, lymphocytes, neutrophils, band cells, monocytes, granulocytes, erythrocytes, eosinophils, basophils or platelets in the human.

5. The method of claim 4 wherein the lymphocytes are T lymphocytes or B lymphocytes.

6. The method of claim 1 wherein the substance P analog is administered by injection.

7. The method of claim 6 wherein the substance P analog is administered intramuscularly.

8. The method of claim 6 wherein the substance P analog is administered subcutaneously.

9. The method of claim 6 wherein the substance P analog is administered intradermally.

10. The method of claim 1 wherein the substance P analog is administered by inhalation.

11. The method of claim 10 wherein the substance P analog is administered intranasally.

12. The method of claim 10 wherein the substance P analog is administered by nebulizer or inhaler.

13. The method of claim 1 wherein administration of the substance P analog results in increased differentiation of high proliferative potential-stem and progenitor cells (HPP-SP cells), colony forming cells-granulocyte, erythroid, macrophage, megakaryocyte cells (CFC-GEMM cells), granulocyte-macrophage-colony forming cells (GM-CFC), megakaryocyte-colony forming cells (Mk-CFC), T-lymphocyte-colony forming cells (T-CFC), B-lymphocyte-colony forming cells (B-CFC), colony forming unit—megakaryocyte cells (CFU-Mk cells), blast forming unit—erythroid cells (BFU-E cells), colony forming unit—erythroid cells (CFU-E cells), or colony forming unit—granulocyte/macrophage cells (CFU-GM cells).

14. The method of claim 13, wherein differentiation of a cell population selected from BFU-E, CFU-E, CFU-GM and CFU-Mk cells is increased.

15. The method of claim 1 wherein administration of the substance P analog results in increased proliferation of high proliferative potential-stem and progenitor cells HPP-SP cells, CFC-GEMM cells, GM-CFC, Mk-CFC, T-CFC, B-CFC, CFU-Mk cells, BFU-E cells, colony forming unit—erythroid cells (CFU-E cells), or colony forming unit—granulocyte/macrophage cells (CFU-GM cells).

* * * * *

SEQUENCE LISTING

```
<160> NUMBER OF SEQ ID NOS: 13

<210> SEQ ID NO 1
<211> LENGTH: 11
<212> TYPE: PRT
<213> ORGANISM: Artificial Sequence
<220> FEATURE:
<223> OTHER INFORMATION: Substance P Analog

<400> SEQUENCE: 1

Arg Pro Lys Pro Gln Gln Phe Phe Gly Leu Met
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (11)..(11)
<223> OTHER INFORMATION: Xaa is Nle
```

<400> SEQUENCE: 2

Arg Pro Lys Pro Gln Gln Phe Phe Gly Leu Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Substance P Analog

<400> SEQUENCE: 3

Arg Pro Lys Pro Gln Gln Phe Phe Pro Leu Met
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (9)..(9)
<223> OTHER INFORMATION: Xaa is MeGly

<400> SEQUENCE: 4

Arg Pro Lys Pro Gln Gln Phe Phe Xaa Leu Met
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Substance P Analog

<400> SEQUENCE: 5

Arg Pro Lys Pro Gln Gln Phe Thr Gly Leu Met
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (7)..(8)
<223> OTHER INFORMATION: Xaa is F(4-Cl)

<400> SEQUENCE: 6

Arg Pro Lys Pro Gln Gln Xaa Xaa Gly Leu Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (11)..(11)
<223> OTHER INFORMATION: Xaa is M(O)

<400> SEQUENCE: 7

Arg Pro Lys Pro Gln Gln Phe Phe Gly Leu Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (9)..(9)
<223> OTHER INFORMATION: Xaa is MeGly
<220> FEATURE:
<221> NAME/KEY: misc_feature
<222> LOCATION: (11)..(11)
<223> OTHER INFORMATION: Xaa is M(O)

<400> SEQUENCE: 8

Arg Pro Lys Pro Gln Gln Phe Phe Xaa Leu Xaa
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (11)..(11)
<223> OTHER INFORMATION: Xaa is M(O2)

<400> SEQUENCE: 9

Arg Pro Lys Pro Gln Gln Phe Phe Gly Leu Xaa
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (9)..(9)
<223> OTHER INFORMATION: Xaa is MeGly
<220> FEATURE:
<221> NAME/KEY: misc_feature
<222> LOCATION: (11)..(11)
<223> OTHER INFORMATION: Xaa is M(O2)

<400> SEQUENCE: 10

Arg Pro Lys Pro Gln Gln Phe Phe Xaa Leu Xaa
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (1)..(1)
<223> OTHER INFORMATION: Xaa is Z1 and Z1 is NH2
<220> FEATURE:
<221> NAME/KEY: misc_feature
<222> LOCATION: (10)..(10)
<223> OTHER INFORMATION: Xaa is MeGly
<220> FEATURE:

```
<221> NAME/KEY: misc_feature
<222> LOCATION: (12)..(12)
<223> OTHER INFORMATION: Xaa is M(O2)
<220> FEATURE:
<221> NAME/KEY: misc_feature
<222> LOCATION: (13)..(13)
<223> OTHER INFORMATION: Xaa is Z2 and Z2 is C(O)NH2

<400> SEQUENCE: 11

Xaa Arg Pro Lys Pro Gln Gln Phe Phe Xaa Leu Xaa Xaa
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (9)..(9)
<223> OTHER INFORMATION: Xaa is MeGly
<220> FEATURE:
<221> NAME/KEY: misc_feature
<222> LOCATION: (11)..(11)
<223> OTHER INFORMATION: Xaa is M(O2)-NH2

<400> SEQUENCE: 12

Arg Pro Lys Pro Gln Gln Phe Phe Xaa Leu Xaa
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Substance P Analog
<220> FEATURE:
<221> NAME/KEY: misc_feature
<222> LOCATION: (1)..(1)
<223> OTHER INFORMATION: Xaa is Z1-Xaa where Z1 is R2N- or RC(O)NR- ;
      and Xaa is Arg, Lys, 6-N methyllysine or (6-N, 6-N) dimethyllysine
<220> FEATURE:
<221> NAME/KEY: misc_feature
<222> LOCATION: (2)..(2)
<223> OTHER INFORMATION: Xaa is Pro or Ala
<220> FEATURE:
<221> NAME/KEY: misc_feature
<222> LOCATION: (3)..(3)
<223> OTHER INFORMATION: Xaa is Lys, Arg, 6-N-methyllysine or (6-N, 6-N)
      dimethyllysine
<220> FEATURE:
<221> NAME/KEY: misc_feature
<222> LOCATION: (4)..(4)
<223> OTHER INFORMATION: Xaa is Pro or Ala
<220> FEATURE:
<221> NAME/KEY: misc_feature
<222> LOCATION: (5)..(5)
<223> OTHER INFORMATION: Xaa is Gln or Asn
<220> FEATURE:
<221> NAME/KEY: misc_feature
<222> LOCATION: (6)..(6)
<223> OTHER INFORMATION: Xaa is Gln or Asn
<220> FEATURE:
<221> NAME/KEY: misc_feature
<222> LOCATION: (7)..(7)
<223> OTHER INFORMATION: Xaa is Tyr, Phe, or Phe substituted with
      chlorine at position 2, 3 or 4
<220> FEATURE:
<221> NAME/KEY: misc_feature
<222> LOCATION: (8)..(8)
<223> OTHER INFORMATION: Xaa is Tyr, Phe, or Phe substituted with
      chlorine at position 2, 3 or 4
<220> FEATURE:
<221> NAME/KEY: misc_feature
```

```
-continued
<222> LOCATION: (9)..(9)
<223> OTHER INFORMATION: Xaa is Gly, Pro, Ala or N-methylglycine
<220> FEATURE:
<221> NAME/KEY: misc_feature
<222> LOCATION: (10)..(10)
<223> OTHER INFORMATION: Xaa is Leu, Val, Ile, Norleucine, Met, Met
      sulfoxide, Met sulfone, N-methylleucine, or N-methylvaline
<220> FEATURE:
<221> NAME/KEY: misc_feature
<222> LOCATION: (11)..(11)
<223> OTHER INFORMATION: Xaa is -Xaa-Z2 where Z2 is -C(O)NR2 or -C(O)OR
      or a salt; and Xaa is Met, Met sulfoxide, Met sulfone, or
      Norleucine

<400> SEQUENCE: 13

Xaa Xaa Xaa Xaa Xaa Xaa Xaa Xaa Xaa Xaa Xaa
1               5                   10
```